US009428791B2

(12) United States Patent
Spitale et al.

(10) Patent No.: US 9,428,791 B2
(45) Date of Patent: Aug. 30, 2016

(54) PROBES OF RNA STRUCTURE AND METHODS FOR USING THE SAME

(71) Applicant: The Board of Trustees of the Leland Stanford Junior University, Palo Alto, CA (US)

(72) Inventors: Robert Carl Spitale, Sunnyvale, CA (US); Peter Joseph Crisalli, Portola Valley, CA (US); Howard Yuan-Hao Chang, Stanford, CA (US); Eric Todd Kool, Stanford, CA (US); Jong Hwa Jung, Albany, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 254 days.

(21) Appl. No.: 13/967,161

(22) Filed: Aug. 14, 2013

(65) Prior Publication Data

US 2014/0154673 A1 Jun. 5, 2014

Related U.S. Application Data

(60) Provisional application No. 61/683,139, filed on Aug. 14, 2012.

(51) Int. Cl.
*C12Q 1/68* (2006.01)
(52) U.S. Cl.
CPC ........ *C12Q 1/68* (2013.01); *Y10T 436/143333* (2015.01)

(58) Field of Classification Search
CPC ........................................................ C12Q 1/68
USPC ......................................................... 435/6.1
See application file for complete search history.

(56) References Cited

U.S. PATENT DOCUMENTS

| | | | |
|---|---|---|---|
| 4,166,902 A | 9/1979 | Ferruti et al. | |
| 2004/0167090 A1 | 8/2004 | Monahan et al. | |
| 2010/0035761 A1 | 2/2010 | Weeks et al. | |
| 2012/0004278 A1 | 1/2012 | Chang et al. | |

OTHER PUBLICATIONS

Roberts; et al., "Chemistry for peptide and protein PEGylation", Adv Drug Deliv Rev (2002), 54(4):459-476.
Weeks; et al., "Exploring RNA Structural Codes with SHAPE Chemistry", Acc Chem Res (2011), 44(12):1280-1291.

*Primary Examiner* — Jezia Riley
(74) *Attorney, Agent, or Firm* — Glenn J. Foulds; Bozicevic, Field & Francis LLP

(57) ABSTRACT

Methods for obtaining structural data from RNA in a sample, and RNA probes for performing the same, are provided. Methods of reversibly modifying RNA is a sample, in vitro or in vivo, and reversible probes for performing the same, are provided. The RNA probes may be SHAPE probes that include aryl or heteroaryl acyl imidazoles. The RNA probes may be reversible probes that include an aryl or heteroaryl ring substituted with a hydroxyl-reactive group and an azido-containing group. Also provided are methods of comparing in vitro and in vivo RNA structural data. Also provided are methods of diagnosing a cellular proliferative disease condition, e.g., by probing HOTAIR RNA. Aspects of the invention further include compositions, e.g., probes and kits, etc., that find use in methods of the invention.

16 Claims, 24 Drawing Sheets

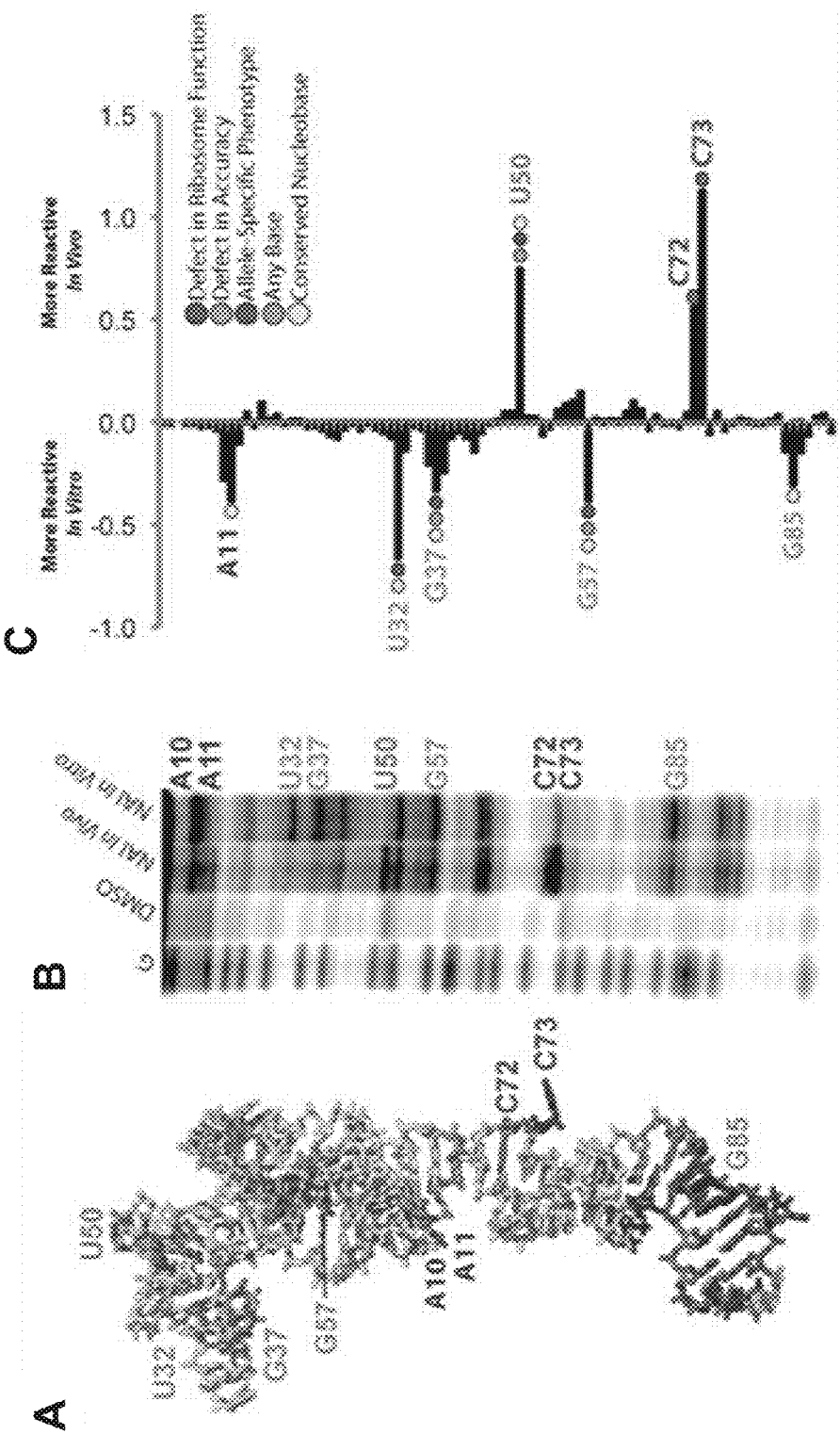

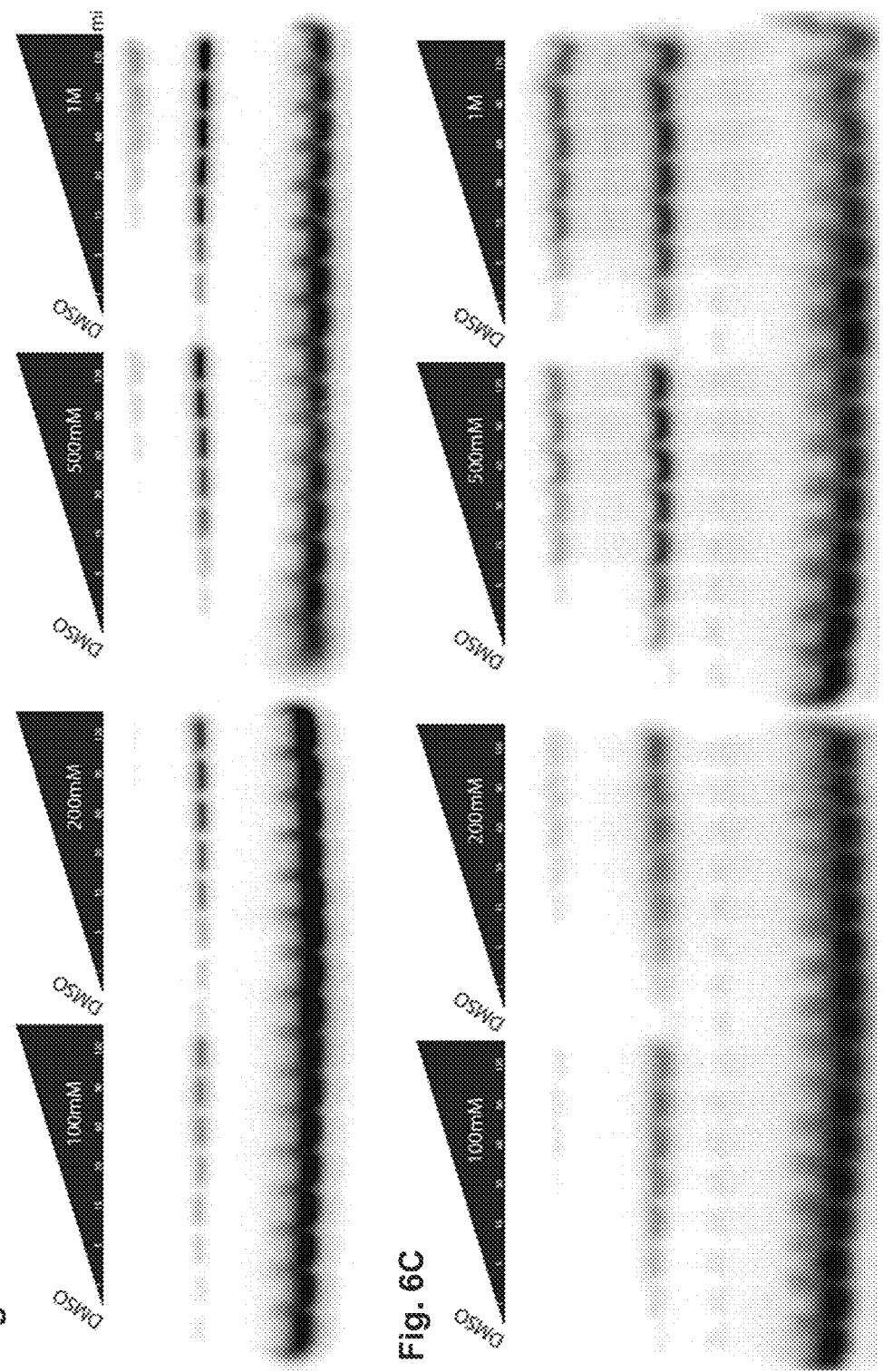

U2 snRNA

SNORD3A

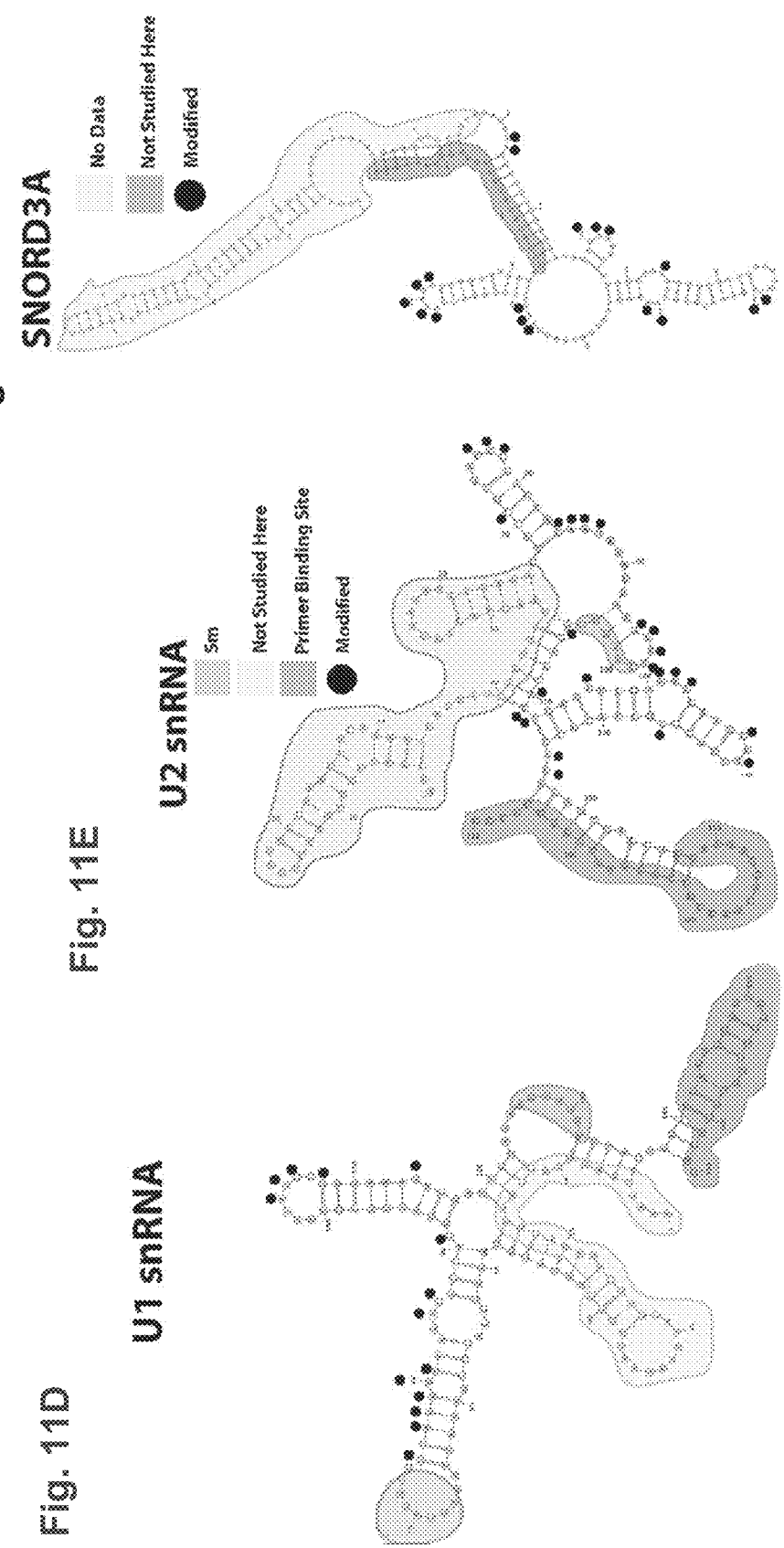

Fig. 16A
1) + Click Control
2) - Click Control
3) + Click Resin, + Click Alexa
4) + Click Resin, + Click Alexa
5) -Click Resin, + Click Alexa
6) - Click Resin, + Click Alexa
Fig. 16B
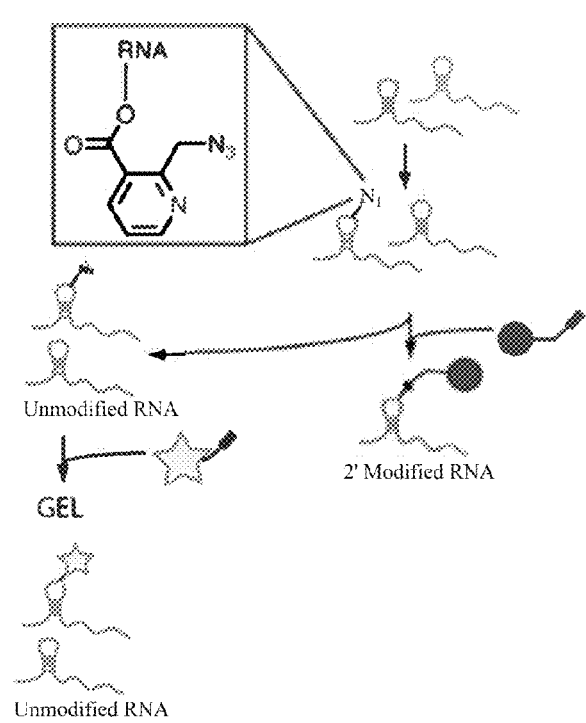
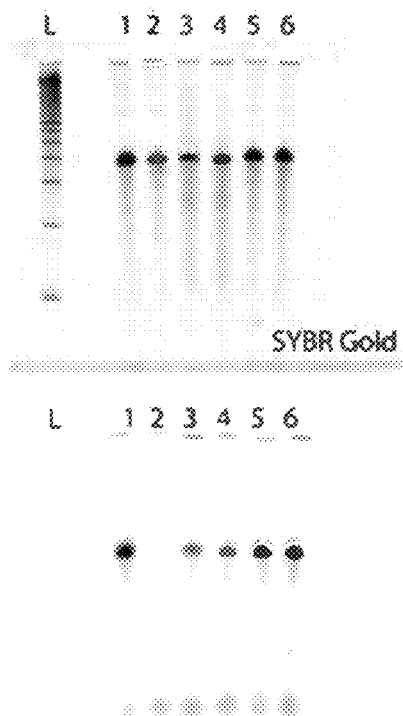

Fig. 17
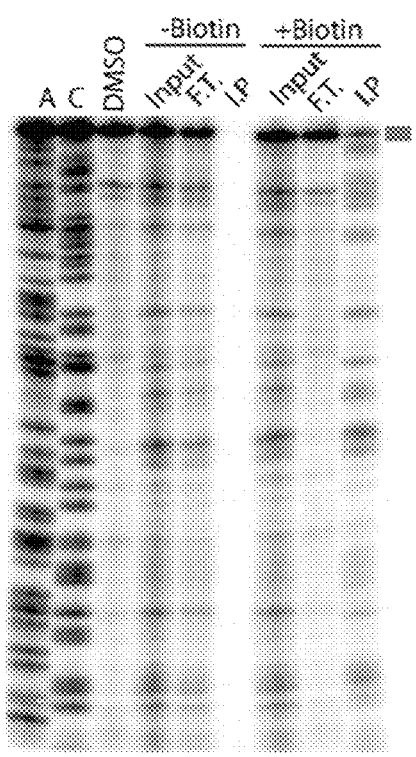
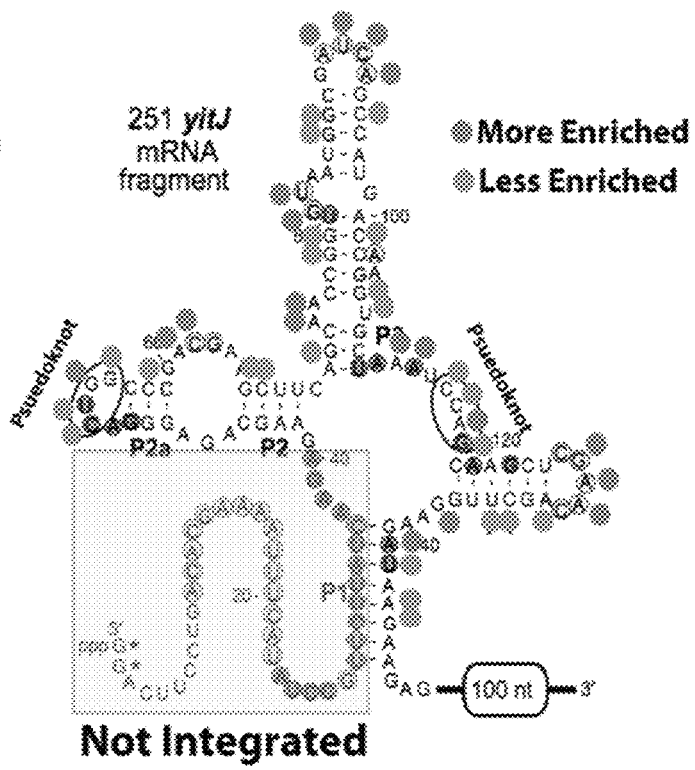

SEQUENCE LISTING

```
<160> NUMBER OF SEQ ID NOS: 19

<210> SEQ ID NO 1
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 1

Asp Pro Asp Pro
1

<210> SEQ ID NO 2
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 2

Asp Pro Asp Pro Asp Pro
1               5

<210> SEQ ID NO 3
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 3

Asp Pro Asp Pro Asp Pro Asp Pro
1               5

<210> SEQ ID NO 4
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 4

Asp Pro Asp Pro Asp Pro Pro
```

```
<210> SEQ ID NO 5
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 5

Asp Pro Asp Pro Pro Asp Pro Pro
1               5

<210> SEQ ID NO 6
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 6

Asp Pro Asp Pro Pro Asp Pro
1               5

<210> SEQ ID NO 7
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 7

Asp Pro Pro Asp Pro Pro Asp Pro
1               5

<210> SEQ ID NO 8
<211> LENGTH: 21
<212> TYPE: DNA
<213> ORGANISM: Artificial sequence
<220> FEATURE:
<223> OTHER INFORMATION: Synthetic nucleic acid sequence

<400> SEQUENCE: 8
aaagcctaca gcacccggta t                                              21

<210> SEQ ID NO 9
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 9
agattgcagc acctgagttt                                                20

<210> SEQ ID NO 10
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 10
tgcctggcag ttccctactc                                                20

<210> SEQ ID NO 11
```

```
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 11
cgaggccaac aacacgcggt                                                    20

<210> SEQ ID NO 12
<211> LENGTH: 24
<212> TYPE: DNA
<213> ORGANISM: Artificial sequence
<220> FEATURE:
<223> OTHER INFORMATION: Synthetic nucleic acid sequence

<400> SEQUENCE: 12
accactcaga ccgcgttctc tccc                                               24

<210> SEQ ID NO 13
<211> LENGTH: 24
<212> TYPE: DNA
<213> ORGANISM: Artificial sequence
<220> FEATURE:
<223> OTHER INFORMATION: Synthetic nucleic acid sequence

<400> SEQUENCE: 13
caggggaaag cgcgaacgca gtcc                                               24

<210> SEQ ID NO 14
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 14
gggtgcaccg ttcctggagg                                                    20

<210> SEQ ID NO 15
<211> LENGTH: 121
<212> TYPE: RNA
<213> ORGANISM: Mus musculus

<400> SEQUENCE: 15
gucuacggcc auaccacccu gaacgcgccc gaucucgucu gaucucggaa gcuaagcagg        60
gucgggccug guuaguacuu ggaugggaga ccgccuggga auaccggguc cuguaggcuu       120
u                                                                       121

<210> SEQ ID NO 16
<211> LENGTH: 164
<212> TYPE: RNA
<213> ORGANISM: Homo sapiens

<400> SEQUENCE: 16
auacuuaccu ggcaggggag auaccaugau cacgaaggug guuucccag ggcgaggcuu         60 auccauugca cuccggaugu gcugaccccu gcgauuuccc caaaugugg aaacucgacu        120 gcauaauuug ugguaguggg ggacugcguu cgcgcuuucc ccug                        164

<210> SEQ ID NO 17
<211> LENGTH: 188
<212> TYPE: RNA
<213> ORGANISM: Homo sapiens
```

```
<400> SEQUENCE: 17
aucgcuucuc ggccuuuugg cuaagaucaa guguaguauc uguucuuauc aguuuaauau      60
cugauacguc cucuauccga ggacaauaua uuaaauggau uuuuggagca gggagaugga     120
auaggagcuu gcuccgucca cuccacgcau cgaccuggua uugcaguacc uccaggaacg     180
gugcaccc                                                             188

<210> SEQ ID NO 18
<211> LENGTH: 217
<212> TYPE: RNA
<213> ORGANISM: Homo sapiens

<400> SEQUENCE: 18
aagacuauac uuucagggau cauuucuaua guguguuacu agagaaguuu cucugaacgu     60
guagagcacc gaaaccacg aggaagagag guagcguuuu cuccugagcg ugaagccggc     120
uuucuggcgu ugcuuggcug caacugccgu cagccauuga ugaucguucu ucucuccgua    180
uuggggagug agagggagag aacgcggucu gaguggu                             217

<210> SEQ ID NO 19
<211> LENGTH: 149
<212> TYPE: RNA
<213> ORGANISM: Artificial sequence
<220> FEATURE:
<223> OTHER INFORMATION: Synthetic nucleic acid sequence

<400> SEQUENCE: 19
ggacuuccug acacgaaaau uucauauccg uucuuaucaa gagaagcaga gggacuggcc    60
cgacgaagcu ucagcaaccg guguaauggc gaucagccau gaccggugcu aaauccagca    120
agcucgaaca gcuuggaaga uaagaagag                                      149
```

PROBES OF RNA STRUCTURE AND METHODS FOR USING THE SAME

GOVERNMENT RIGHTS

This invention was made with Government support under contracts GM072705, GM068122 and HG004361 awarded by the National Institutes of Health. The Government has certain rights in the invention.

INTRODUCTION

Despite being composed of only four chemically similar nucleotides, RNA can base pair with itself and interact with other molecules to form secondary and tertiary structures. In vitro RNA structure-probing has improved the accuracy of secondary structure models and RNA structural motifs. The 2'-hydroxyl group is a universal chemical feature in every RNA. The method of selective 2'-hydroxyl acylation followed by primer extension (SHAPE) has been used to measure and predict the secondary structures of complex RNAs in in vitro systems. Single-stranded or flexible RNA regions exhibit high 2'-hydroxyl reactivity, whereas RNA nucleotides engaged in base pairing or other interactions show lower reactivity.

RNA structure in cells is influenced by the rate of transcription, local solution conditions, the binding of small molecules, and interactions with numerous RNA-binding proteins. Genomes are extensively transcribed to generate diverse coding and regulatory RNAs which play important roles in many facets of gene regulation and in diseases such as cancer. However, many RNAs' structures and functions remain to be characterized in vivo. Probes for elucidating RNA structure and function in cells and in a wide range of organisms to obtain structural maps of RNAs are of interest.

SUMMARY OF THE INVENTION

Methods for obtaining structural data from RNA in a sample, and RNA probes for performing the same, are provided. Methods of reversibly modifying RNA is a sample, in vitro or in vivo, and reversible probes for performing the same, are provided. The RNA probes may be SHAPE probes that include aryl or heteroaryl acyl imidazoles. The RNA probes may be reversible probes that include an aryl or heteroaryl ring substituted with a hydroxyl-reactive group and an azido-containing group. Also provided are methods of comparing in vitro and in vivo RNA structural data. Also provided are methods of diagnosing a cellular proliferative disease condition, e.g., by probing HOTAIR RNA.

In some embodiments the azide functionalized acylation chemicals are functionalized after their conjugation to RNA, e.g. using CLICK chemistry to functionalize with a detectable dye, including fluorescent dyes, to a binding partner, e.g. biotin, digoxin, etc., and the like. The functional group can be used for detection or labeling, for isolation or purification of the tagged RNA, and the like.

In some embodiments the compositions, e.g., probes and kits, etc., are provided that find use in the methods of the invention.

BRIEF DESCRIPTION OF THE DRAWINGS

FIG. 1C shows a time course of ATP modification by NAI and FAI. FIG. 1D shows a correlation of 2'-RNA modification of 5S rRNA in vitro using NAI versus N-methyl isotoic anhydride (NMIA).

FIGS. 5A-5C: (A) Three-dimensional model of S.C. 5SrRNA (PDB 3U5H). (B) Denaturing gel electrophoretic analysis of NAI modification of 5S rRNA in *S. cerevisiae* cells and in vitro. (C) Normalized differential profile of *S. cerevisiae* 5S rRNA. Residues are labeled for their importance in 5S rRNA function as noted in Smith et al., Saturation mutagenesis of 5S rRNA in *Saccharomyces cerevisiae*. Mol Cell Biol 21, 8264-8275, (2001).

FIGS. 6A-6C. Gel shift acylation reactions of NAI and FAI probes: (A) reaction with ATP versus dATP; (B-C) concentration and time course studies with FAI (B); and NAI (C).

FIGS. 11A-11F: NAI modifies nuclear, lower abundant RNAs. (A) Denaturing gel electrophoresis or U1 snRNA RT products. (B) Denaturing gel electrophoresis of U2 snRNA RT products. (C) Denaturing gel electrophoresis of SNORD3A RT products. (D) Secondary structure mapping of U1 snRNA RT products (SEQ ID NO: 16). (E) Secondary structure mapping of U2 snRNA RT products (SEQ ID NO: 17). (F) Secondary structure mapping of SNORD3A snRNA RT products (SEQ ID NO: 18). Secondary structures are represented by theft predicted in vitro folds, not those in their RNP complexes.

FIGS. 16A-16E. NAI-1 was used for conjugation to fluorophores and enrichment handles using "click" chemistry. (A, B) Using the azide-linked acylation reagent fluorescent dye was linked to NAI-1/RNA complexes. (C) Hydroxyls from ATP are acylated. (d) The acylated ATP is supershifted with copper free "click" chemistry with DIBO-biotin. (E) Enrichment for biotin labeled RNAs using a streptavidin pulldown in which the isolated RNAs are eluted then probed using a streptavidin dot-blot.

FIGS. 17A-17B. Functionalized RNA can be enriched to decrease background. (A) Purified RNAs that map back to segments of RNA predicted to be acylated were enriched by functionalizing with biotin through copper-free "click" chemistry, and selection for the biotin tag. (SEQ ID NO: 19).

DEFINITIONS

Figure 1:
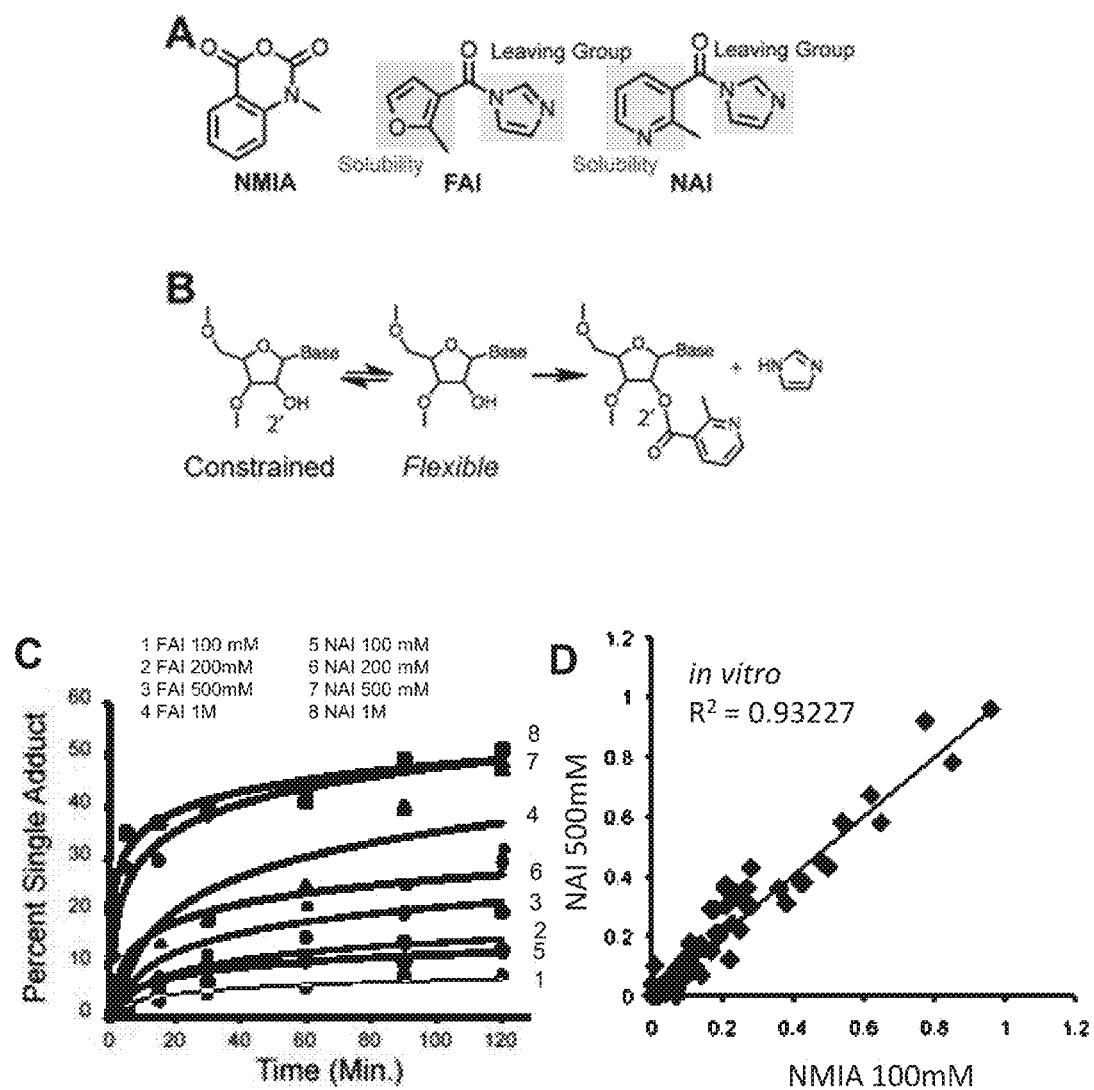
FIGS. 1A-1D depict exemplary probes FAI and NAI (A) and the 2'-O-acylation of a 2'-hydroxyl group of RNA (B).

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. The term lower alkyl will be used herein as known in the art to refer to an alkyl, straight, branched or cyclic, of from about 1 to 6 carbons.

Where substituent groups are specified by their conventional chemical formulae, written from left to right, they equally encompass the chemically identical substituents, which would result from writing the structure from right to left, e.g., —$CH_2O$— is intended to also recite —$OCH_2$—. Use of a single dash ("-") or double dash ("—" or "--") refers to a single covalent bond, while use of "=" refers to a double bond. The symbol,$)_2$ or $_2($, when displayed with —S, indicates that the compound inside the parenthesis may be present as a dimer forming a disulfide bond. The dimer may be reduced to a monomer.

The term "acyl" or "alkanoyl" by itself or in combination with another term, means, unless otherwise stated, a stable straight or branched chain, or cyclic hydrocarbon radical, or combinations thereof, having the stated number of carbon atoms and an acyl radical on at least one terminus of the alkane radical. The "acyl radical" is the group derived from a carboxylic acid by removing the —OH moiety therefrom.

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkylene") and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl", where "heteroalkyl" refers to carbon chains having one or more substitutions at one or more carbon atoms of the hydrocarbon chain fragment. Alkyl groups that are limited to hydrocarbon groups are termed "homoalkyl". Certain alkyl groups include those containing between about one and about twenty five carbon atoms (e.g. methyl, ethyl and the like).

The term "lower alkyl" generally refers to a straight, branched, or cyclic hydrocarbon chain containing 8 or fewer carbon atoms, and can contain from 1 to 8, from 1 to 6, or from 1 to 4 carbon atoms. Certain "lower alkyl" groups include methyl, ethyl, n-propyl, isopropyl, n-butyl, sec-butyl, tert-butyl, n-pentyl, n-hexyl, n-heptyl and the like. "Lower alkyls" can be optionally substituted at one or more carbon atoms of the hydrocarbon chain.

The terms "alkoxy," "alkylamino" and "alkylthio" (or thioalkoxy) are used to refer to those alkyl groups attached to the remainder of the molecule via an oxygen atom, an amino group, or a sulfur atom, respectively.

By "heteroatom" is meant atoms other than a carbon which may be present in a carbon backbone or a linear, branched or cyclic compound. Certain heteroatoms include oxygen (O), nitrogen (N), sulfur (S), phosphorus (P) and silicon (Si). Heteroatoms can be present in their reduced forms, e.g., —OH, —NH, and —SH.

The term "heteroalkyl," by itself or in combination with another term, means, unless otherwise stated, a straight or branched chain, or cyclic carbon-containing radical, or combinations thereof, having the stated number of carbon atoms and at least one heteroatom which can be a member selected from O, N, Si, P and S, wherein the nitrogen, phosphorous and sulfur atoms are optionally oxidized, and the nitrogen heteroatom can optionally be quaternized. Normally heteroalkyl groups contain no more than two heteroatoms linked in sequence. The heteroatom(s) O, N, P, S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Generally, up to two heteroatoms may be consecutive, such as, for example, —$CH_2$—NH—$OCH_3$ and —$CH_2$—O—Si($CH_3$)$_3$.

Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, aromatic moiety that can be a single ring or multiple rings (usually from 1 to 3 rings), which are fused together or linked covalently. The term "heteroaryl" refers to aryl groups (or rings) that contain from one to four heteroatoms which are members selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Certain substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R'''' where each can be independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the embodiments includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O) CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R''', —OC(O)R', —C(O)R', —CO$_2$R', —CONR'R", —OC(O) NR'R", —NR"C(O)R', —NR'—C(O)NR"R''', —NR"C(O)$_2$ R', —NR—C(NR'R"R''')=NR'''', —NR—C(NR'R")= NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$) alkoxy, and fluoro(C$_1$-C$_4$)alkyl, in a number ranging from zero to the total number of open valences on the aromatic ring system; and where R', R", R''' and R'''' can be independently selected from hydrogen, substituted or unsubstituted alkyl, substituted or unsubstituted heteroalkyl, substituted or unsubstituted aryl and substituted or unsubstituted heteroaryl. When a compound of the embodiments includes more than one R group, for example, each of the R groups is independently selected as are each R', R", R''' and R'''' groups when more than one of these groups is present. In the schemes that follow, the symbol X represents "R" as described above.

The term "amino" or "amine group" refers to the group —NR'R" (or N±FlR'R") where R, R' and R" are independently selected from hydrogen, alkyl, substituted alkyl, aryl, substituted aryl, aryl alkyl, substituted aryl alkyl, heteroaryl, and substituted heteroaryl. A substituted amine is an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —N$^+$RR'R" and its biologically compatible anionic counterions.

The compounds of the invention, or their pharmaceutically acceptable salts may contain one or more asymmetric centers and may thus give rise to enantiomers, diastereomers, geometric isomers, individual isomers and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

In some embodiments the RNA modification provides a reactant group for CLICK chemistry reactions (see *Click Chemistry: Diverse Chemical Function from a Few Good Reactions* Hartmuth C. Kolb, M. G. Finn, K. Barry Sharpless Angewandte Chemie International Edition Volume 40, 2001, P. 2004, herein specifically incorporated by reference).

Detailed Description of the Embodiments

As summarized above, methods for obtaining structural data from RNA in a sample, and RNA probes for performing the same, are provided. Methods of reversibly modifying RNA is a sample, in vitro or in vivo, and reversible probes for performing the same, are also provided. The subject RNA probes may be SHAPE probes that include an aryl or heteroaryl ring substituted with an acyl imidazole and a modulating substituent. The subject RNA probes may be reversible probes that include an aryl or heteroaryl ring substituted with a hydroxyl-reactive group and an azido-containing group.

RNA Probes

As summarized above, aspects of the invention include probes of RNA structure. In general terms, the subject RNA probes include a hydroxyl-reactive functional group attached to an aryl or heteroaryl ring where the ring may be further substituted at an adjacent position of the ring with a modulating substituent. The hydroxyl-reactive group is capable of reacting with one of more unconstrained nucleotides of a RNA to produce a 2'-modified RNA. The modulating substituent, if present, modulates the reactivity of the hydroxyl-reactive group. The modulating substituent may be selected to tune the reactivity of the probe to provide a desired reactivity with the 2'-hydroxyl groups of RNA, and a desired stability under physiological conditions, e.g., as measured by half-life and/or minimum incubation times.

Any suitable aryl or heteroaryl ring may be utilized in the subject probes. Aryl and heteroaryl rings of interest include, but are not limited to, phenyl, pyridyl, pyrrolyl, furanyl, thienyl, thiazolyl, imidazolyl, oxazolyl, pyrimidinyl, pyrazinyl and pyridazinyl rings. In some instances, the aryl or heteroaryl ring further comprises one or more groups independently selected from a solubility-enhancing group, a binding moiety, a tag, a detectable label, a permeability-enhancing group and a functional group (e.g., a bioorthogonal group for attaching a detectable label (e.g., a fluorophore) or a solid support). Such groups may be included as part of the ring or in a substituent of the ring. Chemical modifications can be made to the probe to enhance appropriate solubility. In some cases, the solubility-enhancing group is a basic group that may be protonated and charged under physiological conditions. In other cases, the solubility-enhancing group is a polar group (e.g., a heteroatom containing ring or substituent) that is neutral under physiological conditions but which is hydrophilic. In certain instances, the solubility-enhancing group is a basic center (e.g., a N atom) that is part of the heteroaryl ring (e.g., a pyridyl ring). By solubility-enhancing is meant that the solubility of a probe at physiological conditions is increased by the inclusion of the group of interest, relative to a corresponding probe that lacks the solubility-enhancing group. For example, a pyridyl ring has enhanced solubility at physiological pH over a corresponding benzyl ring because it includes a basic nitrogen in the ring. Chemical modifications can be made to the probe to enhance appropriate cell permeability by, e.g., (1) changing the pKa of the probe, (2) adding an ionic permeability-enhancing group, either cationic or anionic, attached through an appropriate linker to the aryl or heteroaryl ring, or (3) adding nonionic permeability-enhancing groups such as ethylene glycol or polyethylene glycol moieties.

Any suitable hydroxyl-reactive groups may be utilized in the subject probes. Hydroxyl reactive groups of interest include, but are not limited to, active esters, epoxides, oxiranes, oxidizing agents, aldehydes, alkyl halides (e.g., benzyl halides), isocyanates, and other groups such as those described by Hermanson, Bioconjugate Techniques, Second Edition, Academic Press, 2008. In some cases, the hydroxyl-reactive group is an active ester. Any convenient active ester group may be utilized in the subject RNA probes. The active ester of the probe may react with one of more uncontrained 2'-hydroxyl groups of an RNA to produce a 2'-acylated RNA. In some instances, the active ester is an acyl imidazole. The acyl imidazole (—C(O)-imidazolyl) group may include an imidazolyl that is further substituted with one or more substituents, including but not limited to, a lower alkyl (e.g., a methyl or ethyl group), a halo (e.g. a bromo, a chloro or a fluoro) and nitro. In certain instances, the imidazolyl group is a 2-methyl-imidazolyl or a 4-methyl-imidazolyl.

Any suitable modulating substituent may be included at the 2-position of the aryl or heteroaryl ring (2-position relative to the hydroxyl-reactive group substituent). By "adjacent position of the ring" is meant that that two ring substituents (e.g., the hydroxyl-reactive group and the modulating substituent) are attached to the ring at consecutive ring positions, i.e., at positions 1- and 2- of a ring, relative to each other. In some instances, the hydroxyl reactive group and modulating substituent are selected to provide for a desired probe reactivity and stability. In some embodiments, the hydroxyl reactive group is acyl imidazole, and the modulating substituent is an alkyl group. The proximity of the modulating substituent, at the adjacent position on the ring to the acyl imidazole, allows the modulating substituent to modulate the reactivity of the acyl imidazole group. Without wishing to be bound by theory, in some cases the modulating substituent may have a steric effect on the acyl imidazole group. In certain instances, the modulating substituent is an alkyl group such as a lower alkyl group, optionally further substituted with one or more substituents.

In some embodiments, the hydroxyl reactive group and the modulating substituent are selected to provide a RNA probe with a desired half-life in the sample, e.g., a half-life of 5 minutes or more, such as 10 minutes or more, 20 minutes or more, 30 minutes or more, 40 minutes or more, 50 minutes or more, 60 minutes or more, 2 hours or more, 3 hours or more, or even 6 hours or more.

In some instances, the modulating substituent is further substituted with a masked group. As used herein, the term "masked group" refers to a group of the probe that can be selectively unmasked to produce an unmasked reactive functional group. A masked group is stable, e.g., to physiological conditions, until it is contacted with a stimulus capable of unmasking the masked group. As such, in some instances, the probe may include a masked group that is unmasked upon application of a stimulus. Any suitable groups may be utilized as a masked group in the subject probes. Groups of interest include, but are not limited to, protected functional groups (e.g., protected nucleophilic groups), convertible functional groups and bioorthogonal groups. As used herein "convertible functional group" refers to a stable functional group that upon application of a suitable stimulus is transformed into a reactive functional group, e.g., a functional group that is capable of reacting spontaneously. As such, unmasking of a masked group may include deprotection, or alternatively, conversion of a stable functional group to a reactive functional group (e.g., a nucleophilic group). The unmasked group may then react spontaneously (e.g., intramolecularly at an adjacent electrophilic center) to reverse modification of the RNA. In some cases, unmasking a masked group includes deprotecting. In certain embodiments, the RNA probe does not include a modulating substituent at the 2-position relative to the hydroxyl-reactive group.

In some embodiments, the RNA probe of the invention is described by formula (I):

where Y is a hydroxyl-reactive group, A is an aryl or a heteroaryl ring, and $R^1$ is H or a lower alkyl.

One aspect of the invention is a SHAPE probe that acylates one or more 2'-hydroxyl groups of a RNA of interest in a sample. As such, in formula (I), Y may include an active ester functional group. Any convenient active ester group may be utilized in the subject SHAPE probes. The active ester of the probe may react with one of more unconstrained nucleotides of a RNA to produce a 2'-acylated RNA. In some instances, the active ester is an acyl imidazole. The acyl imidazole (—C(O)-imidazolyl) group may include an imidazolyl that is further substituted with one or more substituents, including but not limited to, a lower alkyl (e.g., a methyl or ethyl group), a halo (e.g. a bromo, a chloro or a fluoro) and a nitro. In certain instances, the imidazolyl group is a 2-methyl-imidazolyl or a 4-methyl-imidazolyl.

Any convenient aryl or a heteroaryl ring may be utilized in the subject SHAPE probes. In addition to an active ester substituent (e.g., the acyl imidazole group of formula (I)), the aryl or heteroaryl ring may be further substituted, e.g., with a modifying substituent ($R^1$) at the 2-position relative to the active ester.

In some embodiments, a SHAPE probe of the invention is described by formula (II):

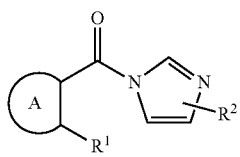

(II)

wherein A is an aryl or a heteroaryl ring; $R^1$ is H or a lower alkyl; and $R^2$ is H, a lower alkyl, a halo or nitro.

In certain instances, in formula (II), A is further substituted at any convenient position, with a functional group that is bioorthogonal, i.e., a functional group that is stable under the physiological conditions of a sample of interest, but which selectively reacts with a complementary reagent (e.g., a detectable label reagent). A variety of bioorthogonal chemistries and reagents may be utilized in the subject probes and reagents, including but not limited to, Staudinger ligations (e.g., using azido and phosphine groups), copper-free click chemistry (e.g., using azido and cyclooctyne groups), oxime or hydrazine chemistry (using aldehydes and ketones). The introduction of such a functional group as a substituent of the aryl or heteroaryl ring (A) allows for the 2'-acylated RNA to be further modified with a moiety such as a detectable label (e.g., a fluorophore or a peptide tag), or a solid support.

In some embodiments, the SHAPE probe is described by one of formulas (III) and (IV):

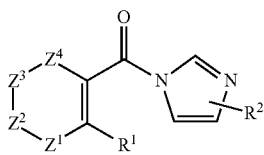

(III)

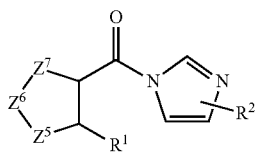

(IV)

where $R^1$ and $R^2$ are as defined above, $Z^1$, $Z^2$, $Z^3$, $Z^4$ $Z^5$, $Z^6$ and $Z^7$ are independently selected from O, S, $CR^3$, N and $NR^3$, and where $R^3$ is H or an aryl group substituent.

In some cases, in formulas (I) to (IV), the probe includes an aryl or heteroaryl ring (A) selected from a phenyl, a pyridyl, a pyrrolyl, a furanyl, a thienyl, a thiazolyl, an imidazolyl, an oxazolyl, a pyrimidinyl, a pyrazinyl and a pyridazinyl ring.

In certain embodiments, the SHAPE probe is described by one of the following structures:

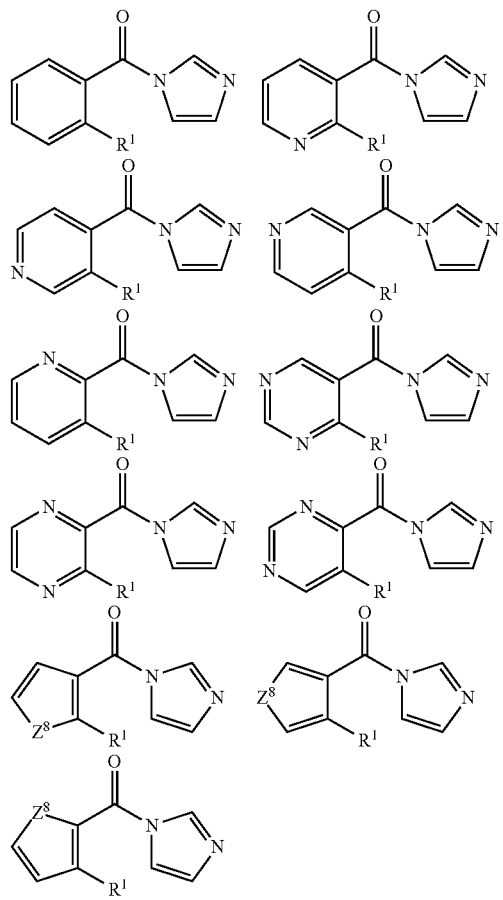

where $R^1$ is as defined above, $Z^8$ is O, S or $NR^4$, wherein $R^4$ is H or a lower alkyl; and where the imidazolyl group of the active ester is optionally substituted with a lower alkyl, a halo or nitro.

In certain embodiments, $R^1$ is a lower alkyl (e.g., a methyl, an ethyl, a propyl, an isopropyl, a butyl, or a tert-butyl). $R^1$ may be further substituted with azido, hydroxyl, thiol, an amino, or a protected version thereof.

In certain embodiments, $R^1$ is selected from one of the following groups:

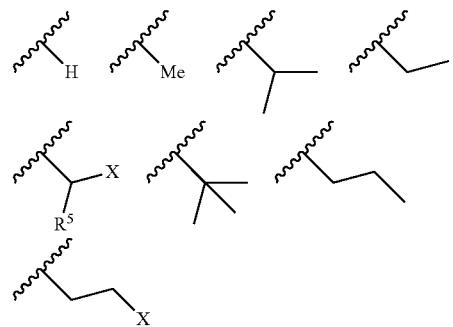

where X is selected from $-N_3$, hydroxyl, protected hydroxyl, thiol, protected thiol, amino and protected amino;

and $R^5$ is H or an alkyl group substituent. In some instances, $R^5$ is H, a lower alkyl, hydroxyl, or an alkyloxy. In certain instances, $R^1$ is $-CH_2-N_3$ or $-CH_2CH_2N_3$.

As summarized above, another aspect of the invention is a reversible RNA probe. In some instances, the probe includes a modulating substituent (e.g., $R^1$) that includes a masked group (e.g., as described herein) such that the probe reversibly modifies RNA. The modification of one or more unconstrained nucleotides of the 2'-modified RNA by the probe may be reversed by the application of a stimulus. Application of the stimulus to the sample unmasks a masked group of the probe which leads to cleavage of the probe from the 2'-modified RNA. In some cases, the 2'-modified RNA is 2'-acylated RNA and application of the stimulus to the sample may be described as de-acylating the 2'-acylated RNA.

By "reversibly modifying" or "reverse modification" is meant that the modification of a RNA in a sample may be reversed upon application of a suitable stimulus that unmasks a masked group of the probe. By "reversibly acylates" is meant that the acylation of a RNA of interest in a sample may be reversed upon application of a suitable stimulus (e.g., a photon, a deprotection reagent or a chemical agent) that unmasks a masked reactive group of the probe. In some cases, the unmasked reactive group may then react intra-molecularly at the adjacent 2'-acyl group to release 2'-hydroxyl RNA.

In certain embodiments, the masked group is an azido group. The azido group may be "unmasked" by reaction with a reagent such as a phosphine or a dithiol. Without wishing to be bound by theory, reaction of the azido group with a phosphine reagent may lead to an iminophosphorane (aza-ylide) intermediate, which can react intramolecularly with an adjacent 2'-acyl electrophilic group to produce a covalent amide bond (see e.g., FIG. 13A).

In some embodiments, the masked group is a functional group protected by a photolabile protecting group. In such cases, the stimulus may be a photon and application of the stimulus photocleaves the masked group to produce a reactive functional group.

In some cases, the reversible probe includes a hydroxyl-reactive group and an azido group linked by an aryl or heteroaryl ring. In some instances, the azido group is included as part of an alkyl substituent (e.g., a $C_1$-$C_6$ alkyl substituent that may be branched or straight chained) of the aryl or heteroaryl ring (e.g., the modulating substituent). In such cases, the azido group is not directly attached to the ring but is attached to a carbon of the substituent that is one or more atoms away from the ring, such as 1, 2 or 3 or more atoms removed from the ring. In other instances, the azido group is directly attached to the ring.

In some cases, the hydroxyl-reactive group and the azido group are attached to the aryl or heteroaryl ring at neighboring positions of the ring (e.g., at the 1- and 2-positions of a ring). In some embodiments, the probe is described by formula (V):

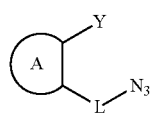 (V)

where Y is a hydroxyl-reactive group; A is an aryl or a heteroaryl ring; and L is a lower alkyl group, optionally substituted with an alkyl group substituent. In certain embodiments, Y is an active ester.

In certain embodiments, A comprises one or more groups independently selected from a solubility-enhancing group, a binding moiety, a permeability-enhancing group, a detectable label and a bioorthogonal group (e.g., for attaching a detectable label (e.g., a fluorophore) or a solid support).

In certain instances, in formula (V), A is further substituted at any convenient position, with a functional group that is bioorthogonal, i.e., a functional group that is stable under the physiological conditions of a sample of interest, but which selectively reacts with a complementary reagent (e.g., a detectable label reagent). A variety of bioorthogonal chemistries and reagents may be utilized in the subject probes and reagents, including but not limited to, Staudinger ligations (e.g., using azido and phosphine groups), copper-free click chemistry (e.g., using azido and cyclooctyne groups), oxime or hydrazine chemistry (using aldehydes and ketones). The introduction of such a functional group as a substituent of the aryl or heteroaryl ring (A) allows for the 2'-modified RNA to be further modified with a moiety such as a detectable label (e.g., a fluorophore or a peptide tag), or a solid support.

In certain embodiments, the reversible probe is described by one of formulas (VI) and (VII):

 (VI)

 (VII)

where: $Z^1$, $Z^2$, $Z^3$, $Z^4$, $Z^5$, $Z^6$ and $Z^7$ are independently selected from O, S, CR, N and NR, where R is H or an aryl group substituent; B and D are aryl or heteroaryl rings; and X is halo, imidazolyl, an N-hydroxylsuccinimidyl (e.g., NHS or sulfo-NHS), an alkoxy (e.g., methoxy) or an aryloxy (e.g., pentafluorophenyloxy); and m is 1 or 2. In formula (VI), $Z^1$, $Z^2$, $Z^3$ and $Z^4$ are selected to provide an aryl or heteroaryl ring. In formula (VII), $Z^5$, $Z^6$ and $Z^7$ are selected to provide an aryl or heteroaryl ring. In certain embodiments, in formulas (VI) and (VII), the B and D rings are aryl or heteroaryl rings selected from a phenyl, a pyridyl, a pyrrolyl, a furanyl, a thienyl, a thiazolyl, an imidazolyl, an oxazolyl, a pyrimidinyl, a pyrazinyl and a pyridazinyl ring.

In some cases, the reversible probe is described by one of the following structures:

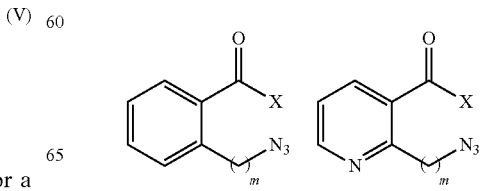

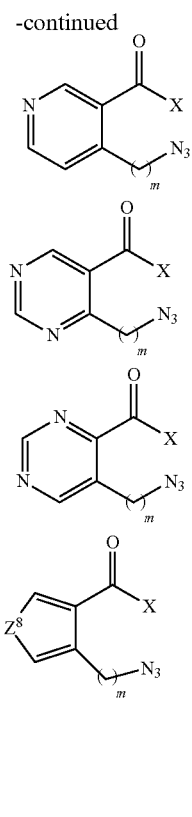

where $Z^8$ is O, S or $NR^4$, wherein $R^4$ is H or a lower alkyl; X is as defined above, and m is 1 or 2.

In certain embodiments, X is an imidazolyl, optionally substituted with a lower alkyl (e.g., a 2-methyl or a 4-methyl), a halo (e.g., a bromo, chloro or fluoro) or nitro. In certain embodiments, m is 1.

Masked Groups

As used herein, the term "masked group" refers to a group of the probe that can be selectively unmasked to produce an unmasked reactive functional group. The masked group may be unmasked after contact with a stimulus (e.g., light, or a chemical agent) under suitable conditions. The modifiable group is capable of modification under conditions at which target molecules of interest are able to be maintained in a native state in a sample (e.g., physiological conditions at which RNA structure is maintained in a cell). The masked group may be unmasked to produce an unmasked group that is capable of spontaneous reaction with an adjacent compatible functional group (e.g., intramolecular or intermolecular).

The masked group may be reactive with the functional group of a chemical agent (e.g., an azido-containing masked group that is reactive with a phosphine reagent or a dithiol). A variety of functional group chemistries and chemical agent stimuli suitable for unmasked them may be utilized in the subject probes and methods. Functional group chemistries and chemical agents of interest include, but are not limited to, Click chemistry groups and reagents (e.g., as described by Sharpless et al., (2001), "Click Chemistry: Diverse Chemical Function from a Few Good Reactions", Angewandte Chemie International Edition 40 (11): 2004-2021), Staudinger ligation groups and reagents (e.g., as described by Bertozzi et al., (2000), "Cell Surface Engineering by a Modified Staudinger Reaction", Science 287 (5460): 2007), and other bioconjugation groups and reagents (e.g., as described by Hermanson, Bioconjugate Techniques, Second Edition, Academic Press, 2008). In certain embodiments, the modifiable group includes a functional group selected from an azido, a phosphine (e.g., a triaryl phosphine or a trialkyl phosphine or mixtures thereof), a dithiol, an active ester, an alkynyl, a protected amino, a protected hydroxy, a protected thiol, a hydrazine, and a disulfide.

In some instances, the masked group includes an azido group, such as those contained in the azido linkers described in US2001/0014611.

The masked group may be cleavable, e.g., include a cleavable bond. As used herein, the term "cleavable" refers to a moiety that includes a cleavable covalent bond that can be selectively cleaved to produce two products. Application of a suitable cleavage stimulus to a probe that contains a cleavable bond will produce two products. As used herein, the term "cleavage conditions" refers to the conditions in which a cleavable bond may be selectively cleaved. Irradiation of a sample with light of a suitable wavelength that is absorbed by a photocleavable group is an example of a cleavage condition. A variety of cleavable protecting groups, linkers and functional groups are known to those of skill in the art and find use in the subject probes, e.g., as described in Olejnik et al. (Methods in Enzymology 1998 291:135-154), and further described in U.S. Pat. No. 6,027,890; Olejnik et al. (Proc. Natl. Acad Sci, 92:7590-94); Ogata et al. (Anal. Chem. 2002 74:4702-4708); Bai et al. (Nucl. Acids Res. 2004 32:535-541); Zhao et al. (Anal. Chem. 2002 74:4259-4268); and Sanford et al. (Chem. Mater. 1998 10:1510-20). Cleavable groups and linkers including the same that may be employed in the subject probes include electrophilically cleavable groups, enzymatically cleavable groups, nucleophilically cleavable groups, photocleavable groups, metal cleavable groups, electrolytically-cleavable groups, and groups that are cleavable under reductive and oxidative conditions. A cleavable group or linker may be selectively cleaved without breaking other cleavable bonds in the molecule.

The masked group may be photoreactive (e.g., reactive with a stimulus such as a photon or light of a particular wavelength). In some instances, the photoreactive group is photocleavable, photoisomerizable (or photoswitchable), or photoactivateable.

In certain embodiments, the masked group includes a photocleavable group, where application of a suitable light stimulus activates the group and leads to intramolecular cleavage of the 2'-modified RNA. Any convenient photocleavable groups may find use in the subject probes. Cleavable groups and linkers may include photocleavable groups comprising covalent bonds that break upon exposure to light of a certain wavelength. Suitable photocleavable groups and linkers for use in the subject probes include ortho-nitrobenzyl-based linkers, phenacyl linkers, alkoxybenzoin linkers, chromium arene complex linkers, NpSSMpact linkers and pivaloylglycol linkers, as described in Guillier et al. (Chem. Rev. 2000 1000:2091-2157). For example, a 1-(2-nitrophenyl)ethyl-based photocleavable linker (Ambergen) can be efficiently cleaved using near-UV light, e.g., in >90% yield in 5-10 minutes using a 365 nm peak lamp at 1-5 mW/cm². In some embodiments, the masked group is a photocleavable group such as a nitro-aryl group, e.g., a nitro-indole group or a nitro-benzyl group, including but not limited to: 2-nitroveratryloxycarbonyl, α-carboxy-2-nitrobenzyl, 1-(2-nitrophenyl)ethyl, 1-(4,5-dimethoxy-2-nitrophenyl)ethyl and 5-carboxymethoxy-2-nitrobenzyl. Nitro-indole groups of interest include, e.g., a 3-nitro-indole, a 4-nitro indole, a 5-nitro indole, a 6-nitro-indole or a 7-nitro-indole group, where the indole ring may be further substituted at any suitable position, e.g., with a methyl group or a halo group (e.g., a bromo or chloro), e.g., at the 3-, 5- or 7-position. In certain embodiments, the nitro-aryl group is a 7-nitro indolyl group.

In some embodiments, the masked group is acid or base labile, e.g., cleavable with an acidic or a basic reagent. In another embodiment, the masked group is pH sensitive, such that application of a stimulus such as a suitable pH condition (e.g., a low pH condition below the isoelectric point of the group) modifies the group, e.g., by changing a neutral group (e.g., an amino or carboxylic acid group) into a charged group (e.g., an ammonium or a carboxylate group). In certain embodiments, the masked group is an acid/base labile group of the structure: —NHC(O)OR$^3$ where R$^3$ is selected from a methyl, ethyl, methoxymethyl, $CH_2CH_2F$, methylthiomethyl, β-glucuronide, β-galacturonide, D-glucopyranosyl, β-D-galactopyranosyl, tetra-O-acetyl-D-glucopyranosyl, and a tetra-O-acetyl-β-D-galactopyranosyl group. In certain instances, the acid labile group is peptide sequence susceptible to cleavage at a pH between pH1 and pH4 (e.g., pH 2-4 or pH 3-4). In certain embodiments, the MCIP includes an acid-cleavable linker as described in US2012/0122153, such as a linker comprising a peptide selected from the group consisting of: (SEQ ID NO: 1) DPDP, (SEQ ID NO: 2) DPDPDP, (SEQ ID NO: 3) DPDPDPDP, (SEQ ID NO: 4) DPDPDPP, (SEQ ID NO: 5) DPDPPDPP, (SEQ ID NO: 6) DPDPPDP, and (SEQ ID NO: 7) DPPDPPDP. In other instances, the acid labile group is a pH sensitive hydrazones (see e.g., Bioconjugate Chem., 2010, 21 (1), pp 5-13 and Clin. Cancer Res. 2005 11(2 Pt 1):843-52).

In some embodiments, the masked group is a protected hydroxyl group, such as a silyl ether group (e.g., —OSiR$_3$). The silyl ether may be unmasked by application of a stimulus such as a chemical agent (e.g., a fluoride reagent) that cleaves the silyl ether and leads to an intramolecular reaction with an adjacent acyl electrophilic center to release 2'-RNA. An exemplary masked group, probe and stimulus is illustrated in the following scheme:

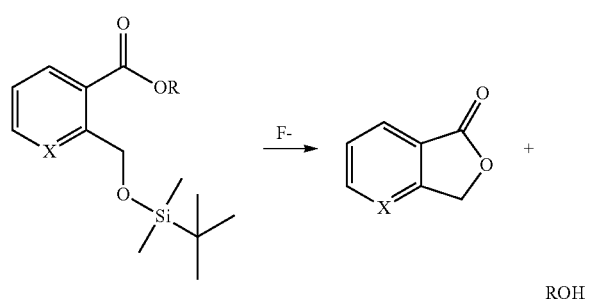

where X is N or CH, and R is RNA.

In some embodiments, the azido-containing masked group is an azido-substituted alkyl ether (e.g., an azido-methylether). The azido-substituted alkyl ether may be unmasked by application of a stimulus such as an azido reactive chemical agent (e.g., a phosphine or dithiol reagent) that converts the azido group to a reactive group (e.g., an amino group) via a Staudinger-type reaction. Without wishing to be bound by theory, unmasking of an azido-methylether group may produce an unstable functional group (e.g., an alpha-amino ether) that spontaneously hydrolyses and leads to intramolecular reaction with an adjacent acyl electrophilic center to release 2'-RNA. An exemplary masked group, probe and stimulus is illustrated in the following scheme:

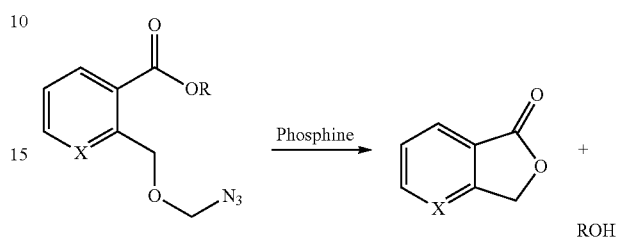

where X is N or CH, and R is RNA.

In some embodiments, the masked group is a protected hydroxyl group that may be used in conjunction with an adjacent hydroxyl reactive group that is trimethyl lock derivative (e.g., an o-hydroxydihydrocinnamic acid derivative). Deprotection of the protected hydroxyl group leads to lactonization with the adjacent electrophilic acyl group to release 2'-RNA. Any convenient trimethyl lock compound may be adapted for use in the subject probes, such as those described by Raines et al. "Trimethyl lock: a trigger for molecular release in chemistry, biology, and pharmacology", Chem. Sci., 2012, 3, 2412-2420, the disclosure of which is herein incorporated by reference. An exemplary masked group, probe and stimulus is illustrated in the following scheme:

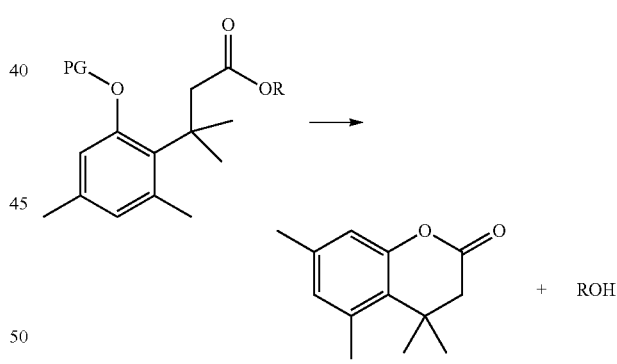

where PG is a hydroxyl protecting group and R is RNA.

Methods

As summarized above, aspects of the invention include methods for obtaining structural data from a RNA in a sample. Further aspects of the invention include methods for reversibly modifying RNA in a sample. The subject methods include modifying one or more unconstrained nucleotides of the RNA to produce a 2'-modified RNA. In some cases, modification of the RNA includes acylation to produce a 2'-acylated RNA. In other cases, modification does not include acylation, e.g, when using probes including hydroxyl-reactive groups that are not active esters (e.g., as described herein). In such cases, modification may include an alkylation or addition reaction of a 2'-hydroxy of the RNA of interest.

As such, aspects of the method include contacting the sample with a RNA probe under conditions by which one or more unconstrained nucleotides of the RNA are modified by the probe to produce a 2'-modified RNA. Any convenient protocol for contacting the sample with the probe may be employed. The particular protocol that is employed may vary, e.g., depending on whether the sample is in vitro or in vivo. For in vitro protocols, contact of the sample with the probe may be achieved using any convenient protocol. In some instances, the sample includes cells that are maintained in a suitable culture medium, and the probe is introduced into the culture medium. For in vivo protocols, any convenient administration protocol may be employed. Depending upon the reactivity of the probe, the RNA of interest, the manner of administration, the half-life, the number of cells present, various protocols may be employed. The term "sample" as used herein relates to a material or mixture of materials, typically, although not necessarily, in fluid form, containing one or more components of interest.

The subject methods may further include evaluating the sample modification of the RNA. Evaluation of the sample may be performed using any convenient method, and at any convenient time. Evaluation of the sample may be performed continuously, or by sampling at one or more time points during the subject method. In some embodiments, the evaluating step is performed prior to obtaining structural data. In certain cases, evaluation is performed using a cell-based assay that measures the occurrence of a biological event triggered by the RNA. In other cases, evaluation is performed in conjunction with obtaining structural data. Any observable biological property of interest may be used in the evaluating step of the subject methods.

The subject methods may further include analyzing the 2'-acylated RNA in the sample to obtain structural data. Selective 2'-hydroxyl acylation followed by primer extension (SHAPE) is a method for obtaining structural data from a RNA. Any suitable SHAPE methods and reagents may be utilized in practicing the subject methods. SHAPE methods and reagents of interest include, but are not limited to, those described by Weeks and Mauger, "Exploring RNA Structural Codes With SHAPE Chemistry", Accounts of Chemical Research, 2011, 44 (12), 1280-1291; and Weeks et al. US 2010/0035761, the disclosures of which are herein incorporated by reference.

Once the RNA of interest has been 2'-modified in a sample (e.g., as evaluated by the occurrence of a particular biological event), the modification may be maintained for a period of time, and/or may be reversed via application of a stimulus to the sample.

Aspects of the methods include applying a suitable stimulus to reverse modification of the 2'-modified RNA. Any suitable stimulus may be utilized to reverse modification of the 2'-modified RNA by a reversible probe of the invention. In some instances, the stimulus is a photon. In other instances, the stimulus is a chemical agent (e.g., a deprotection agent or an azido-reactive agent).

In some instances, the stimulus is a deprotection reagent and application of the stimulus deprotects a protected functional group of the probe, such as a protected amino, hydroxyl or thiol. In other instances, the stimulus is an azido-reactive reagent, and application of the stimulus modifies an azido group of the probe, e.g., via a Staudinger-type reaction. Any suitable azido-reactive reagents may be utilized as a stimulus. Azido-reactive reagents of interest include, but are not limited to, dithiols and phosphines such as, arylphosphines (e.g., a triphenyl phosphine), alkylphosphines (e.g., a trialkylphosphine such as tris(2-carboxyethyl) phosphine (TCEP)), or arylalkylphosphines.

In certain embodiments, the stimulus is application of a chemical agent, where the chemical agent is bound to a solid support. Any convenient supports and methods may be utilized, including but not limited to, chromatographic supports and methods, arrays, beads, etc.

Application of a chemical agent stimulus can be achieved using any convenient method, including contacting the sample with the chemical agent using any convenient method. The particular protocol that is employed may vary, e.g., depending on whether the sample is in vitro or in vivo. For in vitro protocols, contact of the chemical agent with the sample may be achieved using any convenient protocol. In some cases, a solution of the chemical agent is added to the sample to provide a final concentration of the chemical agent in the sample sufficient to modify the RNA of interest. In some instances, the sample includes cells that are maintained in a suitable culture medium, and the chemical agent is introduced into the culture medium. For in vivo protocols, any convenient administration protocol may be employed. Depending upon the reactivity of the chemical agent, the response desired, the manner of administration, the half-life or stability of the chemical agent, the number of cells present, various protocols may be employed.

In some embodiments, the stimulus is a photon. Any suitable source of light may be used in the subject methods for application of the stimulus. Light sources suitable for use in the subject methods include, but are not limited to, UV lamps (e.g., a xenon flash lamp) and laser light sources (e.g., ultraviolet lasers) that irradiate light at an appropriate wavelength suitable for absorption by the probe. In certain cases, application of the stimulus occurs via fluorescence resonance energy transfer (FRET) from a donor chromophore. Laser light sources include the frequency-doubled ruby laser, which produces a, e.g., 200 mJ pulse at 347 nm in 50 ns, and a nitrogen laser (producing e.g., 200 mJ at 337 nm), where sufficient intensity can be achieved by focusing the light through a microscope objective. Any suitable lasers may be configured to produce brief (ns) pulses of monochromatic light of intensity sufficient to modify a probe in a sample. Xenon flash lamps produce a broad spectrum, from 250 to 1500 nm, and may produce pulses of about 1 ms. Filters may be placed in the light path to narrow the spectrum and remove wavelengths (e.g., <300 nm). In certain cases, after filtering, the total output of the lamp may between about 300 and about 400 nm (e.g., between about 320 nm to about 380 nm, between about 330 nm to about 370 nm, or between about 340 nm to about 360 nm) can be configured to produce between about 50 mJ and about 250 mJ (e.g., about 200 mJ) light of intensity sufficient to modify a probe in a sample.

The light source may have a spectral energy distribution suitable for the particular photoactive group (e.g., photolabile, photoisomerizable or photocleavable group) being used in conjunction with the probe. In some cases, photolytic cleavage of a masked group is dependent on the wavelength of the irradiating light, its intensity and duration. For example, long-wave UV, i.e., UV-A, which has spectral energy in the range of about 320-400 nanometers (nm), is suitable for cleaving o-nitrobenzyl groups. A bulb providing a light intensity at the sample in the range of about 0.2 to about 10 mW/cm$^2$ at 365 nm with a 10 nm bandpass may be suitable for such purposes. Light sources of interest include, but are not limited to: chemists' mercury spot lamps with 110 watts BL9 phosphorescent bulbs, 100 W xenon arc lamp which is passed through Hoya 340 and Schott WG 305 filters before illuminating the sample, one or more flashes (e.g., a 50-ns flash) from a frequency-doubled ruby laser that delivers 347 nm light with an average energy of 90 mJ (range 83-104 mJ).

It should be understood that the aforementioned wavelength range may be selected as a compromise between using shorter wavelengths that may damage components of the sample (e.g., wavelengths below 300 nm) and using longer wavelengths that may be less effective at, e.g., cleaving the masked group (e.g., wavelengths above 500 nm). Light having other spectral energy distributions may be required for cleaving other photocleavable linkers. Such other energy distributions are readily available, or can be readily determined using any convenient method.

A variety of methods for supplying uniform illumination, controlling illumination intensity, controlling illumination time, controlling sample temperature, and spatiotemporal control of illumination may be used. As used herein, the terms illumination and irradiation are used interchangeably. In some embodiments, the illumination time is about 30 sec or more, such as about 1 minute or more, about 2 minutes or more, about 3 minutes or more, about 5 minutes or more, about 10 minutes or more, about 20 minutes or more, about 30 minutes or more, about 60 minutes or more, or even more. In certain embodiments, the illumination time includes flash photolysis pulses from a laser of nanosecond, picosecond or femtosecond pulse width. The light source may be directed onto the sample using any convenient method. In some cases, the light source is directed via the optical path of a microscope, where the light can be controlled spatially (e.g., by focusing the light into a small spot at a particular location).

Any suitable methods may be used to evaluate the reversal of modification of the 2'-modified RNA, including but not limited to, primer extension methods, sequencing methods and analytical methods. Evaluation may include comparing the results obtained before and after reversal of modification.

Once modification of the 2'-modified RNA (or particular nucleotides thereof) has been reversed, the RNA may be further analyzed using any convenient method. In some cases, the subject methods is traceless, e.g., the RNA can be returned to its natural unmodified state after reversing modification. In general terms, 2'-modification of RNA renders it unresponsive to cloning methods, e.g, cloning methods used to construct sequencing libraries. As such, reversible modification of the RNA by the subject methods retains the opportunity to perform further analysis and/or sequencing of RNAs of interest, e.g., by reverse transcription polymerase chain reaction (RT-PCR) methods. In addition, probes that include photoreactive groups are amenable to spatiotemporal control of the reversal of modification by control of the application of the stimulus (e.g., light).

Detectable Label Reagent

The subject methods may further include a conjugation step where a functional group of the probe (e.g., a bioorthogonal group substituent of the aryl or heteroaryl ring) may be utilized to further modify the 2'-modified RNA with a modifying moiety. Modifying moieties of interest include but are not limited to, specific binding moieties (e.g., small molecules, biotin, peptides, proteins, etc.), and detectable labels.

In some cases, the method includes contacting the sample with a detectable label reagent under conditions sufficient to produce a labeled 2'-modified RNA. Any convenient methods can be utilized to conjugate a detectable label reagent to the 2'-modified RNA.

As used herein, a "detectable label reagent" refers to an agent that includes a detectable label and a functional group capable of selectively reacting with a probe in a sample. Any convenient functional groups may be used in the subject detectable label reagents. In some cases, the functional group is a bioorthogonal group, such as a group that is capable of selectively reacting with a compatible functional group under physiological conditions. A variety of bioorthogonal chemistries and functional groups may be utilized in the subject detectable label reagents, including but not limited to, Staudinger ligation chemistries and groups (e.g., azido and phosphine groups), copper-free click chemistries and groups (e.g., azido and cyclooctyne groups), oxime or hydrazine chemistries (using aldehydes and ketones). Introduction of such a functional group as a substituent of the aryl or heteroaryl ring (A) allows for the 2'-acylated RNA to be further modified with a moiety such as a detectable label (e.g., a fluorophore or a peptide tag) or a solid support. Functional group chemistries and chemical agents of interest include, but are not limited to, Click chemistry groups and reagents (e.g., as described by Sharpless et al., (2001), "Click Chemistry: Diverse Chemical Function from a Few Good Reactions", Angewandte Chemie International Edition 40 (11): 2004-2021), Staudinger ligation groups and reagents (e.g., as described by Bertozzi et al., (2000), "Cell Surface Engineering by a Modified Staudinger Reaction", Science 287 (5460): 2007), and other bioconjugation groups and reagents (e.g., as described by Hermanson, Bioconjugate Techniques, Second Edition, Academic Press, 2008).

As used herein, a "detectable label" generally refers to an identifying tag that can provide for a detectable signal, e.g., luminescence (e.g., photoluminescence (e.g., fluorescence, phosphorescence), chemoluminescence (e.g., bioluminescence), microparticle aggregation or formation, radioactivity, immunodetection, enzymatic activity, and the like.

"Fluorophore" refers to a molecule that, when excited with light having a selected wavelength, emits light of a different wavelength, which may emit light immediately or with a delay after excitation. Fluorophores, include, without limitation, fluorescein dyes, e.g., 5-carboxyfluorescein (5-FAM), 6-carboxyfluorescein (6-FAM), 2',4',1,4,-tetrachlorofluorescein (TET), 2',4',5',7',1,4-hexachlorofluorescein (HEX), and 2',7'-dimethoxy-4',5'-dichloro-6-carboxyfluorescein (JOE); cyanine dyes, e.g. Cy3, CY5, Cy5.5, QUASAR™ dyes etc.; dansyl derivatives; rhodamine dyes e.g. 6-carboxytetramethylrhodamine (TAMRA), CAL FLUOR™ dyes, tetrapropano-6-carboxyrhodamine (ROX). BODIPY fluorophores, ALEXA™ dyes, Oregon Green, pyrene, perylene, benzopyrene, squarine dyes, coumarin dyes, luminescent transition metal and lanthanide complexes and the like. The term fluorophores includes excimers and exciplexes of such dyes.

Complementary oligonucleotide probes may also be utilized in the subject methods, e.g., oligonucleotides that have complementary sequences capable of selectively hybridizing to a site of interest in the RNA. In some cases, a complementary oligonucleotide probe may be used in conjunction with a chemical agent stimulus in a templated reaction to direct reversal of modification of the 2'-modified RNA to a desired nucleotide of the RNA. In other cases, a complementary oligonucleotide probe may be used in conjunction with a modifying moiety such as a detectable label reagent. Any convenient methods may be used to link a complementary oligonucleotide probe and a chemical agent or modifying moiety. Methods of interest include those described by Shibata et al. "Oligonucleotide-Templated Reactions for Sensing Nucleic Acids", Molecules, 2012, 17, 2446-2463.

Utility

The RNA probes and methods of the invention, e.g., as described above, find use in a variety of applications. Applications of interest include, but are not limited to: research applications and diagnostic applications. Methods of the invention find use in a variety of different applications including any convenient application where a biological process may be modulated by the structure of a RNA of interest. In such cases, the subject probes and methods may be used to obtain structural data of the RNA of interest that finds use in research of the biological process, or in the diagnosis of a disease condition associated with the biological process.

Also of interest is any application where a RNA target can be reversibly modified. A variety of RNA targets may be utilized in the subject methods, including but not limited to, viral RNA, ribosomal RNA (e.g., 5S or 28S rRNA), messenger RNA, telomerase RNA, aptamers, HOTAIR RNA.

Due to the reversible modification of RNA by the subject probes, the methods described herein can be traceless, e.g., the RNA (or particular nucleotides thereof), can be returned to an unmodified state after performing the subject methods. In general terms, 2'-modification of RNA renders the RNA unresponsive to cloning methods, e.g., methods used to construct sequencing libraries. As such, the subject methods find use in any application where the opportunity to perform further analysis and sequencing of RNAs is of interest, e.g., after structural data has been obtained from the RNAs. In addition, probes that include photoreactive groups find use in applications where spatiotemporal control of the reversal of modification by control of the application of the stimulus (e.g., light), is of interest.

Comparison of In Vitro and In Vivo RNA Structural Data

Aspects of the invention include methods for comparing in vitro and in vivo RNA structural data. The subject methods may include: contacting an in vitro sample comprising a first RNA, with a first RNA probe to acylate one or more unconstrained nucleotides of the first RNA to produce a first 2'-acylated RNA, and analyzing the first 2'-acylated RNA to obtain in vitro structural data; contacting an in vivo sample comprising a second RNA with a second RNA probe to acylate one or more unconstrained nucleotides of the second RNA to produce a second 2'-acylated RNA in vivo, and analyzing the 2'-acylated RNA to obtain in vivo structural data; and comparing the in vitro structural data with the in vivo structural data.

In some embodiments, the method further comprises identifying one or more nucleotides of the RNA that are differentially acylated in vitro versus in vivo. The subject methods find use in elucidating differences in the structure of RNA in vivo versus in vitro. The subject methods find use in elucidating sites of the RNA structure that are involved in interactions with other biomolecules in the sample. In some embodiments, the in vitro sample is a control sample to which a variety of control components may be added, e.g., biomolecules, or fragments thereof, which are known to interact which the RNA of interest. In such methods, the components of the control sample may be selected to probe one or more interactions of the RNA with biomolecules of interest in the non-control sample.

The subject methods can be adapted for use in comparing RNA structural data between any two first and second samples, to identify differences between the RNA structure and/or function. The first and second samples may both be of the same type (e.g., both in vivo samples or both in vitro samples). Any two samples of interest can be compared using the subject methods.

The first and second RNA probes may be independently any convenient RNA probe (e.g., as described herein). In the subject methods, the first and second RNA probes may each be independently described by formula (I):

where A is an aryl or heteroaryl ring; $R^1$ is H or a lower alkyl; and Y is a hydroxyl-reactive group. In certain instances, Y is an active ester (e.g., an acyl imidazole). In some cases, $R^1$ further comprises an azido group. The aryl or heteroaryl ring A may further comprise a bioorthonal group. The bioorthogonal group may be any suitable functional group that is stable under physiological conditions but which is capable of reacting with a suitable detectable label reagent. Any convenient chemistries may be utilized to add a detectable label to a 2'-modified RNA of interest.

Diagnosis of a Disease Condition

The subject compounds and methods find use in a variety of diagnostic applications, including but not limited to, the development of clinical diagnostics, e.g., in vitro diagnostics or in vivo diagnostics where the structure and/or function of a RNA of interest is implicated. Such applications are useful in diagnosing or confirming diagnosis of a disease condition, or susceptibility thereto, determining the proper course of treatment for a patient suffering from a disease condition. The methods are also useful for monitoring disease progression and/or response to treatment in patients who have been previously diagnosed with the disease. Diagnostic applications of interest include diagnosis of disease conditions, such as those conditions described above, including but not limited to: cancer, inhibition of angiogenesis and metastasis, cancer-related pain, metastatic breast cancer, etc.

Any suitable methods may be used to perform the subject methods of diagnosing a disease condition. Methods of interest that may be adapted are necessary for practicing the subject methods include, but are not limited to, sample extraction and preparation methods, detection and quantification methods, RT-PCR methods, normalization methods, etc.

Aspects of the invention include methods of diagnosing a cellular proliferative disease condition. The subject methods may include: contacting a cell comprising a RNA with a RNA probe under conditions sufficient to acylate one or more unconstrained nucleotides of the RNA to produce a 2'-modified RNA; and evaluating the 2'-modified RNA to diagnose the presence or absence of a cellular proliferative disease condition.

In some embodiments, the RNA is HOTAIR RNA. In the subject methods, the first and second RNA probes may each be independently described by formula (I):

where A is an aryl or heteroaryl ring; $R^1$ is H or a lower alkyl; and Y is a hydroxyl-reactive group. In certain embodiments, Y is an active ester (e.g., an acyl imidazole).

In some embodiments, $R^1$ further comprises an azido group. The aryl or heteroaryl ring A may further comprise a bioorthogonal group (e.g., as described above).

Kits

Aspects of the invention further include kits, where the kits include one or more components employed in methods of the invention, e.g., RNA probes, RNAs of interest, buffers, SHAPE analysis reagents, stimulus-applying components, detectable label reagents, and cells, as described herein. In some embodiments, the subject kit includes a RNA probe (e.g., as described herein) and one or more components selected from a modification buffer, a stimulus-applying component and a detectable label reagent.

A variety of components suitable for use in analyzing RNA (e.g., by SHAPE analysis) may find use in the subject kits. Any of the components described herein may be provided in the kits. For example, components suitable for use in application of stimuli (i.e., stimulus-applying components), components suitable for use in structural analysis of RNA, including but not limited to, components for RNA sequencing by reverse transcriptase PCR, components for chemical methods of RNA analysis such as SHAPE analysis, e.g., buffers, cells, complementary DNA primers, enzymes such as reverse transcriptases, N-methylisotoic anhydride (NMIA) or 1-methyl-7-nitroisatoic anhydride (1M7) probes, etc. The subject kits may further comprise additional reagents which are required for or convenient and/or desirable to include in the reaction mixture prepared during the subject methods, where such reagents include reagents and buffers for RNA analysis; reagents for adding a detectable label; columns; and the like. Kits may also include tubes, buffers, etc., and instructions for use. The various reagent components of the kits may be present in separate containers, or some or all of them may be pre-combined into a reagent mixture in a single container, as desired.

In some embodiments, the kit finds use in the reversible modification of RNA, the kit comprising a reversible probe of the invention; and a stimulus-applying component, such as a light source or a reagent for unmasking a masked group of the reversible probe.

The stimulus-applying component may be any suitable component (e.g., equipment, a chemical or biological agent) that finds use in the application of a stimulus to a sample (e.g., irradiation of light or contact with a chemical agent). In certain cases, the stimulus-applying component is a UV light source, or a chemical agent. The chemical agent may be supplied in any convenient form, including but not limited to, a lyophilized solid or a solution.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form of these instructions is a computer readable medium, e.g., diskette, compact disk (CD), etc., on which the information has been recorded. Yet another form of these instructions that may be present is a website address which may be used via the internet to access the information at a removed site.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric General Methods and Materials Although, the following protocols are described for probes NAI and FAI, the protocols can be adapted for use with any suitable probe.

Synthetic Methods. 2-methylnicotinic acid, 2-methyl-3-furoic acid and 1,1'-carbonyldiimidazole are purchased from Sigma-Aldrich and used as received. Anhydrous dimethylsulfoxide (DMSO) is purchased from Acros Organics and used as received. NMR is performed on a Varian 500 MHz instrument and all spectra referenced to the residual solvent peak.

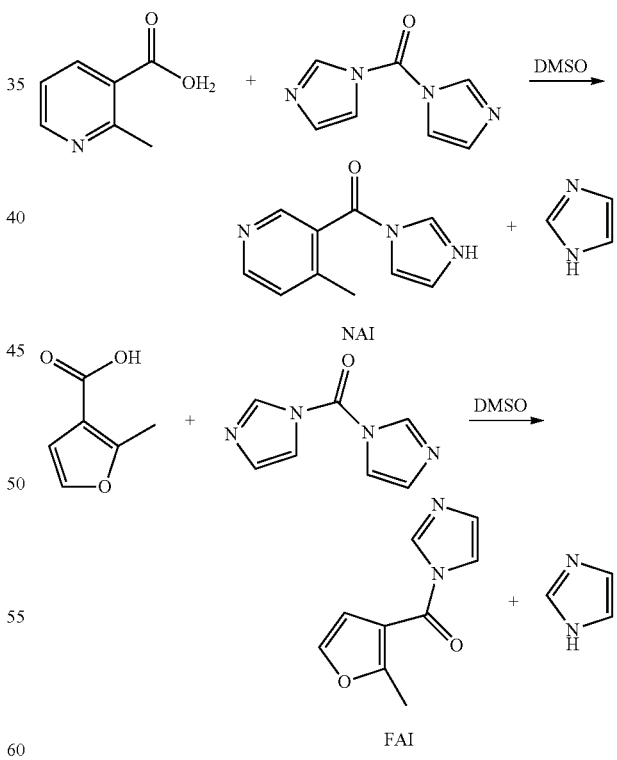

2-methylnicotinic acid imidizolide (NAI). 137 mg (1 mmol) 2-methylnicotinic acid is dissolved in 0.5 mL anhydrous DMSO. A solution of 162 mg (1 mmol) 1,1'-carbonyldiimidazole in 0.5 mL anhydrous DMSO is added dropwise over 5 minutes. The resulting solution is stirred at room temperature until gas evolution is complete, then stirred at room temperature for one hour. The resulting solution is used as a 1.0 M stock solution (assuming complete conversion) containing a 1:1 mixture of the desired compound and imidazole. The solution is frozen at −80° C. when not in use. An analytical sample is prepared by use of dichloromethane as solvent instead of DMSO. The crude reaction is purified by flash silica column chromatography, eluting with ethyl acetate.

$^1$H NMR (500 MHz, CDCl$_3$): 2.61 (s, 3H), 7.15 (s, 1H), 7.30 (m, 1H), 7.42 (s, 1H), 7.73 (dd, 1H, J=8 Hz, 2 Hz), 7.88 (s, 1H), 8.72 (dd, 1H, J=5 Hz, 2 Hz); $^{13}$C NMR (125 MHz, CDCl$_3$): 23.0, 117.2, 120.6, 127.8, 131.6, 135.9, 137.6, 152.1, 157.1, 165.2; HRMS (Calc M+H=188.0818): 188.0819.

2-methyl-3-furoic acid imidazolide (FAI). 126 mg (1 mmol) 2-methyl-3-furoic acid is dissolved in 0.5 mL anhydrous DMSO. A solution of 162 mg (1 mmol) 1,1′-carbonyldiimidazole in 0.5 mL anhydrous DMSO is added dropwise over 5 minutes. The resulting solution is stirred at room temperature until gas evolution is complete, then further stirred at room temperature for one hour. The resulting solution is used as a 1.0 M stock solution (assuming complete conversion) containing a 1:1 mixture of the desired compound and imidazole. The solution is frozen at −80° C. when not in use. An analytical sample is prepared by use of dichloromethane as solvent instead of DMSO. The crude reaction is purified by flash silica column chromatography, eluting with 1:1 hexanes:EtOAc. NMR indicates the presence of some hydrolyzed material (identical to the furoic acid starting material).

$^1$H NMR (500 MHz, CDCl$_3$): 2.60 (s, 3H), 6.63 (d, 1H, J=2 Hz), 7.16 (s, 1H), 7.39 (d, 1H, J=2 Hz), 7.55 (s, 1H), 8.20 (s, 1H); $^{13}$C NMR (125 MHz, CDCl$_3$): 13.9, 110.3, 111.1, 117.5, 130.5, 137.5, 140.5, 141.5, 162.3; HRMS (Calc M+Na=199.0478): 199.0481.

Characterization of NAI and FAI Reactivity with ATP

ATP gel shift. Although, the following protocol is described for ATP, the protocols can be adapted for use with any suitable RNA. ATP gel shift reactions are carried out as described by Weeks et al., "RNA structure analysis at single nucleotide resolution by selective 2′-hydroxyl acylation and primer extension (SHAPE)." J. Am. Chem. Soc. 127, 4223-4231, (2005). Briefly, 10,000 cpm/uL of radiolabeled ATP is incubated with increasing amounts of NAI or FAI (10% final volume) in 100 mM HEPES buffer, pH 8.0, containing 6 mM MgCl$_2$, 100 mM NaCl. Reactions are stopped by addition of an equal volume of Gel Loading Buffer 11 (Ambion, Inc.) and placed on ice. Reactions are loaded onto 30% native polyacrylamide gels (29:1 acrylamide:bisacrylamide, 1% TBE) and visualized by phosphorimaging (STORM, Molecular Dynamics). Single adduct reaction rates and percentages are calculated by integrating bands (Image Quant, IM Support) and fit to a single exponential.

Quenching ATP reaction with β-mercaptoethanol (BME). 10,000 cpm/uL of radiolabeled ATP is either preincubated (+) or not (−) with BME final concentration 700 mM in 100 mM HEPES buffer, pH 8.0, containing 6 mM MgCl$_2$, 100 mM NaCl. Immediately after the addition of BME, NAI or FAI (10% final volume) is added and the solution incubated for 5 minutes at room temperature. Reactions are stopped by addition of an equal volume of Gel Loading Buffer 11 (Ambion, Inc.) and placed on ice. Gel images are integrated as above.

Quenching of acylation reactions. An optional quench step is performed for probes having extended reactivity by adapting methods as are used for other RNA modification procedures. See e.g., Zaug, A. J. & Cech, T. R. Analysis of the structure of Tetrahymena nuclear RNAs in vivo: telomerase RNA, the self-splicing rRNA intron, and U2 snRNA. RNA 1, 363-374 (1995). This step allows the experimenter to terminate the reaction at will and perform precise time-course experiments.

Hydrolysis of NAI and FAI. Hydrolysis of NAI and FAI is monitored by adding 1.5 μL of a 100 mM solution of either NAI or FAI in spectroscopic grade DMF to 598.5 μL of buffer (100 mM HEPES, 100 mM NaCl, 10 mM MgSO$_4$, pH 8.0) and monitoring the decrease in absorbance at 265 nm (NAI) or 275 nm (FAI). Three parameter pseudo-first order exponential decay kinetics are fit using OriginPro 8.0 software using the equation:

$$f = y0 + a^* \exp(-b^* x)$$

| Compound | b | Half-Life (Min) |
| --- | --- | --- |
| FAI | .009451 | 73.34 |
| NAI | .020476 | 33.86 |

The $r^2$ for each fit is greater than 0.999

Characterization of NAI and FAI Reactivity with RNA

Acylation of RNA, in vitro. In a typical in vitro modification protocol, 6 μg total RNA is heated in metal-free water for two minutes at 95° C. The RNA is then flash-cooled on ice. The RNA 3× SHAPE buffer (333 mM HEPES, pH 8.0, 20 mM MgCl$_2$, 333 mM NaCl) is added and the RNA allowed to equilibrate at 37° C. for ten minutes. To this mixture, 1 μL of 10× electrophile stock in DMSO (+) or DMSO (−) is added. The reaction is permitted to continue until the desired time. Reactions are quenched with 60 μL of DMS stop solution (0.5 M β-mercaptoethanol, 0.75 M Na.acetate, pH 5.5). Reactions are extracted once with acid phenol:chloroform (pH 4.5±0.2) and twice with chloroform. RNA is precipitated with 40 μL of 3M sodium acetate buffer (pH 5.2) and 1 μL of glycogen (20 ug/uL). Pellets are washed twice with 70% ethanol and resuspended in 10 μL RNase-free water.

Acylation of RNA in mouse embryonic stem cells. Although, the following protocol is described for mouse embryonic stem cells, the protocol can be adapted for use with any suitable cells, V6.5 mouse embryonic stem cells are grown under feeder-free conditions as described by Niwa et al. ("Quantitative expression of Oct-3/4 defines differentiation, dedifferentiation or self-renewal of ES cells." Nat, Genet. 24, 372-376, 2000) and Zhang et al, ("Post-translational modification of POU domain transcription factor Oct-4 by SUMO-1." FASEB J 21, 3042-3051, 2007), Cells are washed 3× with PBS, then scraped and spun down at 700 rpm for 5 minutes. Cells (~3–6×10$^7$) are resuspended in PBS, and DMSO (−), 10% final concentration, or electrophile DMSO (+) is added to the desired final concentration, Cells suspensions are placed at 37° C. and reacted for the desired time. Reactions are terminated with β-mercaptoethanol at 0.7 M final Concentration and reacted at 37° C. for an additional 5 minutes. Cells are then spun down and decanted. To the pelleted cells, 1 mL of trizol LS (Ambion, Inc.) is added, followed by 200 uL of chloroform. RNA is precipitated following the trizol LS manufacturer's instructions. RNA is resuspended to a concentration of 3 ug/10 uL. Reverse transcription primer used for mouse 5S rRNA: 5-AAAGCCTACAGCACCCGGTAT (SEQ ID NO: 8).

Acylation of RNA in human MDA-MB-231 cells. Although, the following protocol is described for human MDA-MB-231 cells, the protocol can be adapted for use with any suitable cells, MDA-MB-231 cells are grown in D-MEM (high glucose) culture medium supplemented with 10% fetal bovine serum (FBS) 0:1 mM MEM NonEssential Amino Acids (NEAA), 2 mM L-glutamine, 1% Pen-Strep. Cells are washed 3× with PBS, then scraped and spun down at 700 rpm for 5 minutes. Cells (~3–6×10$^7$) are resuspended in PBS, and DMSO (−), 10% final concentration, or electrophile in DMSO (+) is added to the desired final concentration. Cells suspensions are placed at 37° C. and reacted for the desired time. Reactions are terminated with β-mercaptoethanol at 0.7 M final concentration and reacted at 37° C. for an additional 5 minutes. Cells are then spun down and decanted. To the pelleted cells, 1 mL of trizol LS (Ambion, Inc.) is added, followed by 200 uL of chloroform. RNA is precipitated following the trizol LS manufacturer's instructions. Pellets are washed twice with 70% ethanol and resuspended in 10 uL RNase-free water. Reverse transcription primer used for human 5S rRNA: 5'-aaagcctacagcac-ccggtat (SEQ ID NO:8).

Acylation of RNA in yeast cells. Although, the following protocol is described for yeast cells, the protocol can be adapted for use with any suitable cells. Yeast cells are grown to an OD$_{600}$ of 1.0 at 30° C. in YPD medium. Cells are spun down at 4000×g and decanted. Cells are resuspended in PBS, and DMSO (−), 10% final concentration, or electrophile in DMSO (+) is added to the desired final concentration. Cell suspensions are placed at 37° C. and reacted for the desired time. Reactions are terminated with β-mercaptoethanol at 0.7 M final concentration and reacted at 37° C. for an additional 5 minutes. Cells are then spun down, decanted, and flash frozen in liquid nitrogen. Frozen pellets are resuspended in 500 uL of 50 mM NaOAc pH5.0, 10 mM EDTA pH 8.0 and 100 uL of 10% SDS. To the mixture 700 uL of saturated phenol is added. Cells are incubated at 65° C. for 1 minute. The freeze thaw cycle is repeated three times. The aqueous phase is separated with PCI(phenol:chloroform:isoamyl alcohol=50:48:2. The aqueous phase is extracted twice with chloroform and added to 3 volumes of ethanol and one-tenth volume of 3M NaOAc pH 5.0. Pellets are washed twice with 70% ethanol and resuspended in 10 UL RNase-free water, Reverse transcription primer used for yeast 5S rRNA: 5'-AGATTGCAGCACCTGAGTTT (SEQ ID NO: 9).

Acylation of RNA in E. coli cells. Although, the following protocol is described for E. coli cells, the protocol can be adapted for use with any suitable cells. E. coli cells are grown to an OD$_{600}$ of 0.25 at 37° C. in YPD medium. Cells are spun down at 4000×g and decanted. Cells are resuspended in PBS, and DMSO (−), 10% final concentration, or electrophile in DMSO (+) is added to the desired final concentration. Cells suspensions are placed at 37° C. and reacted for the desired time, Reactions are terminated with β-mercaptoethanol at 0.7 M final concentration and reacted at 37° C. for an additional 5 minutes, Cells are then spun down, decanted, and flash frozen in liquid nitrogen. Cells are resuspended in a final volume of a fresh solution of 800 µl 0.5 mg/ml lysozyme, TE pH 8.0. 80 µl of 10% SDS is added to the mixture and the slurry is placed at 64° C. for 1-2 min. After incubation add 88 µl 1 M NaOAc, pH5.2 is added. The samples are added to an equal volume (1 ml) of water-saturated phenol (pH <7.0) and incubated at 64° C. for 6 min. The resultant slurry is spun at max speed (14,000 rpm) for 10 min at 4° C. The aqueous phase is extracted twice with chloroform and added to 3 volumes of ethanol and one-tenth volume of 3M NaOAc pH 5.0. Pellets are washed twice with 70% ethanol and resuspended in 10 µL RNase-free water. Reverse transcription primer used for E. coil 5S rRNA: 5'-TGCCTGGCAGTTCCCTACTC (SEQ ID NO: 10).

Acylation of RNA in Drosophila S2 cells, Although, the following protocol is described for Drosophila S2 cells, the protocol can be adapted for use with any suitable cells. Drosophila S2 cells are grown at 25° C. in Schneider's Drosophila Medium (Invitrogen, Carlsbad, Calif.) supplemented with 10% Fetal Bovine serum (SAFC Biosciences, Lenexa, Kans.) and Penicillin-Streptomycin (Invitrogen, Carlsbad, Calif.). Cells are washed 3× with PBS, then scraped and spun down at 700 rpm for 5 minutes. Cells (~3–6×10$^7$) are resuspended in PBS, and DMSO (−), 10% final concentration, or electrophile in DMSO (+) is added to the desired final concentration. Cells suspensions are placed at 37° C. and reacted for the desired time. Reactions are terminated with β-mercaptoethanol at 0.7 M final concentration and reacted at 37° C. for an additional 5 minutes. Cells are then spun down and decanted. To the pelleted cells, 1 mL of trizol LS (Ambion, Inc.) is added, followed by 200 µL of chloroform. RNA is precipitated following the trizol LS manufacturer's instructions. Pellets are washed twice with 70% ethanol and resuspended in 10 µL RNase-free water, Reverse transcription primer used for Drosophila 5S rRNA: 5'-CGAGGCCAACAACACGCGGT (SEQ ID NO: 11).

Acylation and enrichment for nuclear RNAs in HeLa S3 cells. Although, the following protocol is described for HeLa S3 cells, the protocol can be adapted for use with any suitable cells. HeLa S3 cells are grown in D-MEM (high glucose) culture medium supplemented with 10% fetal bovine serum (FBS) 0.1 mM MEM NonEssential Amino Acids (NEAA), 2 mM L-glutamine, 1% Pen-Strep. Cells are washed 3× with PBS, then scraped and spun down at 700 rpm for 5 minutes. Cells (~3–6×10$^7$) are resuspended in PBS, and DMSO (−), 10% final concentration, or 2M electrophile (200 mM final) in DMSO (+) is added to the desired final concentration. Cell suspensions are placed at 37° C. and reacted for thirty minutes, Reactions are terminated with β-mercaptoethanol at 0.7 M final concentration and reacted at 37° C. for an additional 5 minutes. Cells are then spun down and decanted. HeLa cell pellets are resuspended in 2 ml PBS, 2 ml nuclear isolation buffer (1.28 M sucrose; 40 mM Tris-HCl pH 7.5; 20 mM MgCl2; 4% Triton X-100), and 6 ml water on ice for 20 min (with frequent mixing). Nuclei are pelleted by centrifugation at 2,500 G for 15 min. Nuclear pellet is resuspended in 1 ml RIP buffer (150 mM KCl, 25 mM Tris pH 7.4, 0.5 mM DTT, 0.5% NP40, 1 mM PMSF), Resuspended nuclei are mechanically sheared using a dounce homogenizer with 15-20 strokes, Nuclear membrane and debris are pelleted by centrifugation at 13,000 RPM for 10 min. To the mixture 700 µL of saturated phenol is added. Cells are incubated at 65° C. for 10 minutes. The aqueous phase is separated with PCI (phenol:chloroform:isoamyl alcohol 50:46:2). The aqueous phase is extracted twice with chloroform and added to 3 volumes of ethanol and one-tenth volume of 3M NaOAc pH 5.0. Pellets are washed twice with 70% ethanol and resuspended in 10 RNase-free water. *Homo sapiens* small nucleolar RNA, C/D box 3A (SNORD3A), RT Primer: ACCACTCAGACCGCGTTCTCTCCC (SEQ ID NO: 12). *Homo sapiens* RNA, U1 small nuclear 1 (RNU1-1), small nuclear RNA TR Primer: CAGGGGAAAGCGC-GAACGCAGTCC (SEQ ID NO:7) (SEQ ID NO:13). *Homo sapiens* RNA, U2 small nuclear 1 (RNU2-1), small nuclear RNA RT Primer: GGGTGCACCGTTCCTGGAGG (SEQ ID NO:14).

Reverse Transcription of modified RNA (in vivo and in vitro). $^{32}$P-end-labeled DNA primers are annealed to 3 μg of total RNA by incubating at 95° C. for two minutes followed by a step-down cooling (2 deg/sec) to 4° C. To the reaction first-strand buffer, DTT and dNTPs are added. The reaction is pre-incubated at 52° C. for one minute, then superscript III (2 units/4 final concentration) is added. Extensions are performed for ten minutes. To the reaction, 1 μL of 4 M NaOH is added and allowed to react for 5 minutes. 10 μL of Gel Loading Buffer II (Ambion, Inc.) is then added, and cDNA extensions are resolved on 8% denaturing (7 M Urea) polyacrylamide gels (29:1 acrylamide:bisacrylamide, 1% TBE).

Characterization of reverse transcription stops. cDNA extensions are visualized by phosphorimaging (STORM, Molecular Dynamics). cDNA bands are integrated with SAFA[4]. SHAPE reactivities are normalized to a scale spanning 0 to ~1.5, where 1.0 is defined as the mean intensity of highly reactive nucleotides. RNA secondary structures are predicted using mFOLD software.

Results

Screening of acylation electrophiles. Several acylation electrophiles (Table 1) were screened for selective reactivity toward hydroxyl groups, solubility at high concentrations, and amenability to RNA modification inside living cells within a reasonable time frame. Qualitative results are shown in Table 1.

| Compound | Result |
| --- | --- |
| 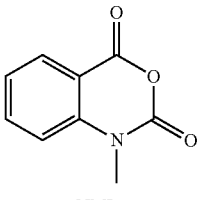 NMIA | Control |
| 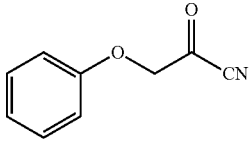 phenoxyacetyl cyanide | Too Reactive, High Hydrolysis |
| 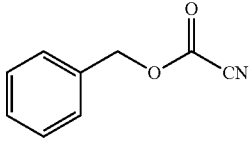 benzyl cyanoformate | Too Reactive, High Hydrolysis |
| 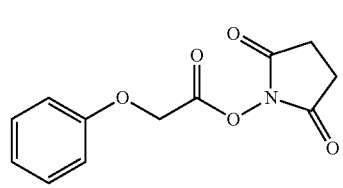 phenoxyacetic acid NHS ester | Low ATP Modification |
| 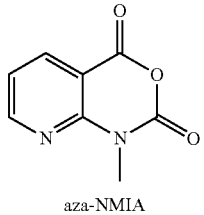 aza-NMIA | Too Reactive, High Hydrolysis |
| 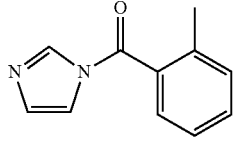 methylbenzoyl-imidazole | Good ATP Modification, Low Solubility |
| 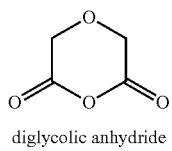 diglycolic anhydride | Weak ATP Modification. |
| 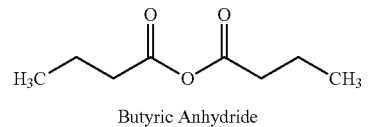 Butyric Anhydride | Unreactive, Low Solubility |
| 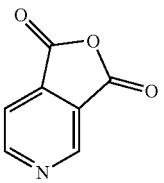 3,4-Pyridinedicarboxylic anyhydride | Low ATP Modification |
| 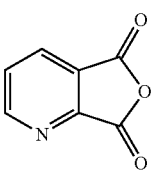 2,3-Pyridinedicarboxylic anhydride | Low ATP Modification |

Figure 3:
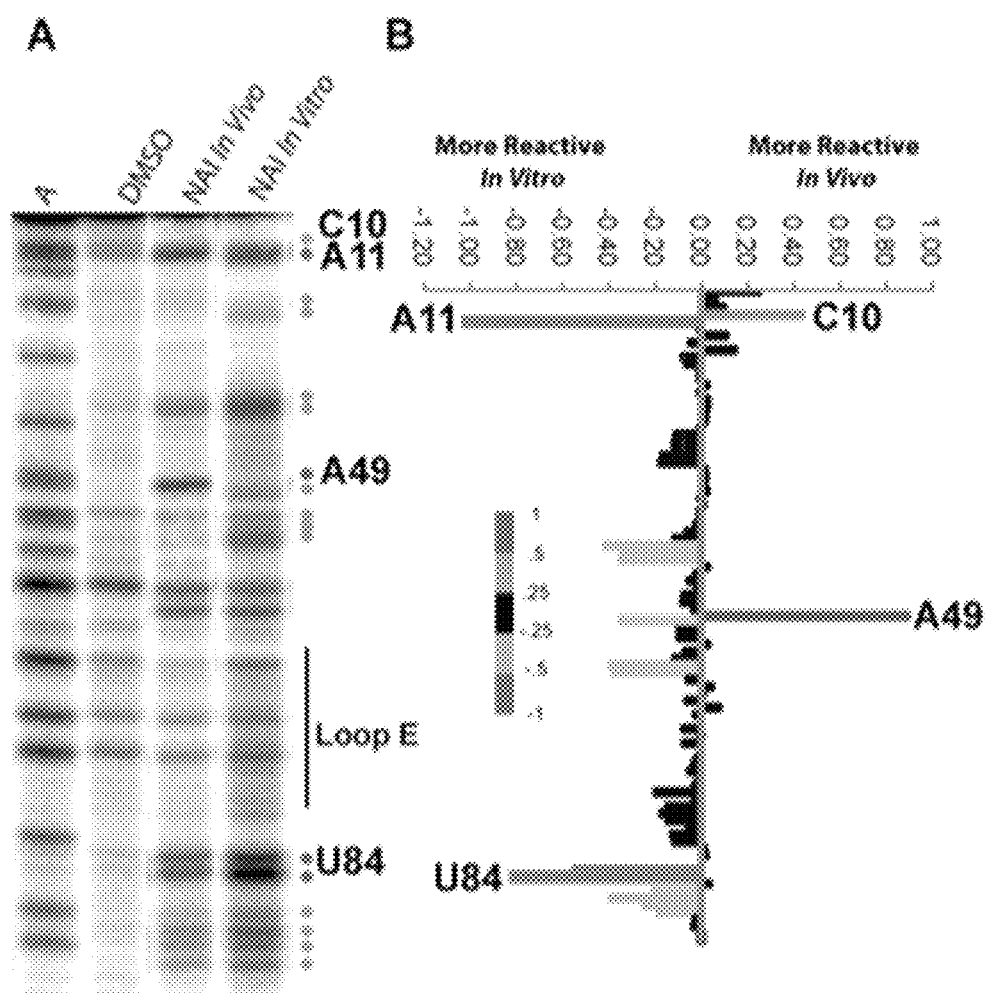
FIGS. 3A-3B illustrate that 5S rRNA has different modification patterns in cells: (A) denaturing gel electrophoretic analysis of NAI modification of 5S rRNA in *M. musculus* Embyronic Stem cells and in vitro; and (B) normalized Differential profile of *M. musculus* Embryonic Stem cell 5S rRNA.

Evaluation of exemplary probes NAI and FAI. Both NAI and FAI were reactive with ATP as illustrated in FIG. 3 using methods as described above. Both NAI and FAI were found to retain reactivity with ATP at 120 minutes in aqueous buffer, whereas NMIA is mostly quenched after thirty minutes (see Weeks et al., J. Am. Chem. Soc. 127, 4223-4231, 2005). The rate of hydrolysis was evaluated using methods described herein and it was observed that NAI ($t_{1/2}$ hydrolysis=33 min) and FAI ($t_{1/2}$ hydrolysis=73 min) are considerably more stable in aqueous solution in comparison to NMIA ($t_{1/2}$ hydrolysis=4 min, see Weeks et al.).

Figure 7:
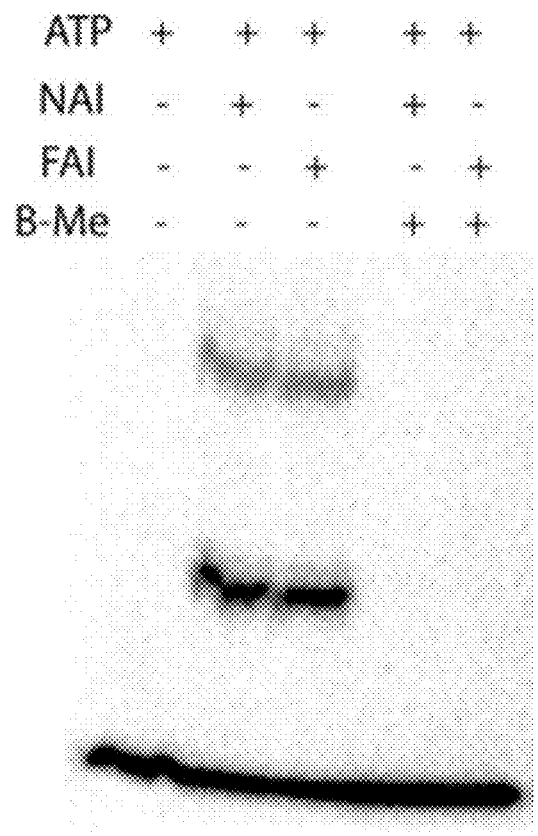
FIG. 7 illustrates the gel shift results of quenching of acylation reactions of NAI and FAI with ATP using β-mercaptoethanol (B-Me).
Figure 8A:
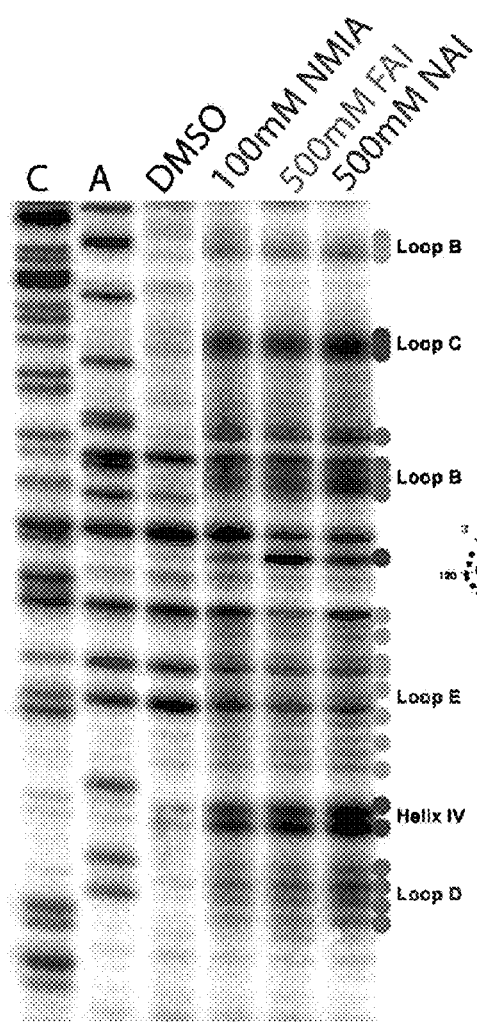
FIGS. 8A-8H, Characterization of probe reactivity with 5S RNA. (A) Gel electrophoresis comparing reactivities of NMIA, FM, and NAI. (B) Secondary structure map to *Mus. Musculus* 5S rRNA (SEQ ID NO: 15). (C) Normalized SHAPE reactivity for NMIA from (A). (D) Normalized SHAPE reactivity for FAI from (A). (E) Normalized SHAPE reactivity for NAI from (A). (F) Correlation of position-dependent reactivities of NMIA and NAI. (G) Comparison between NMIA and FAI. (H) Comparison between NAI and FAI.
Figure 8B:
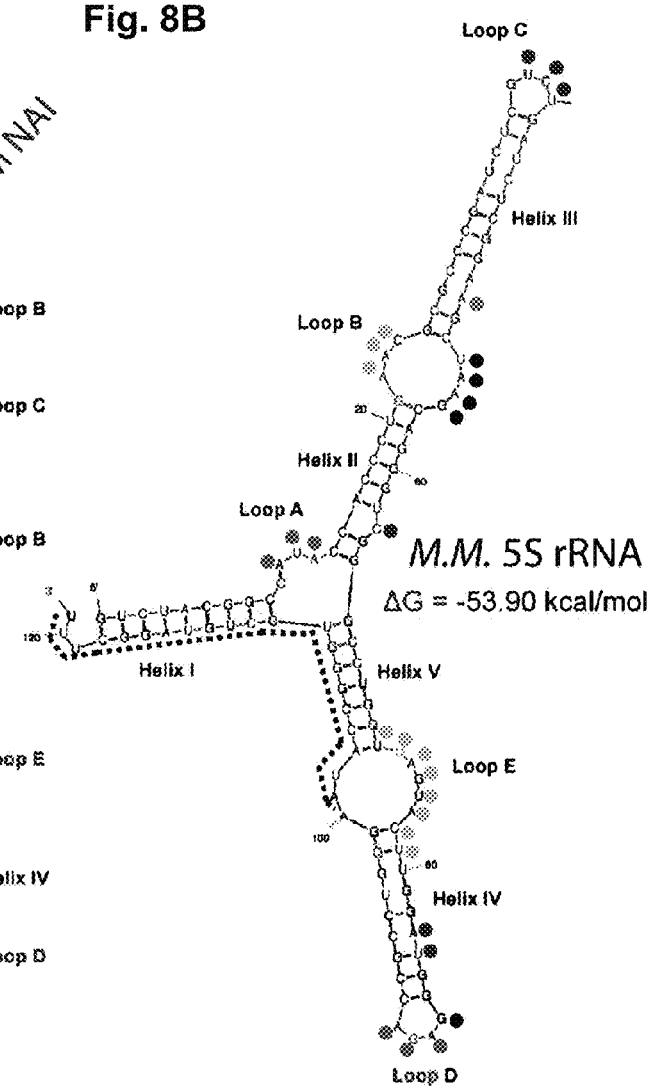
Figure 8C:
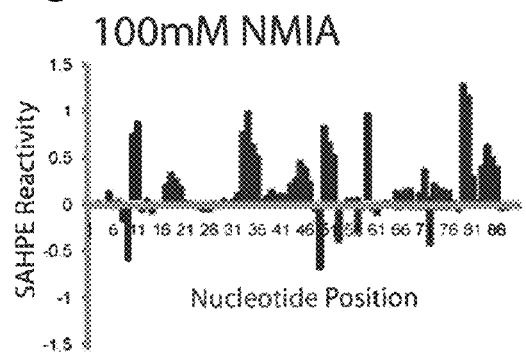
Figure 8F:
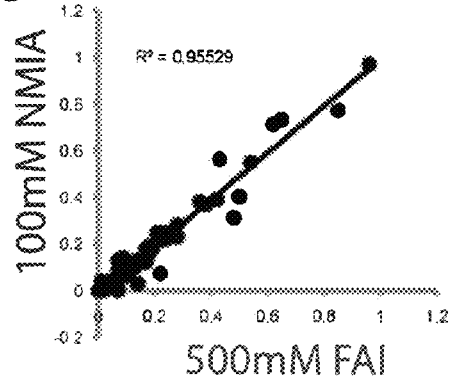
Figure 8D:
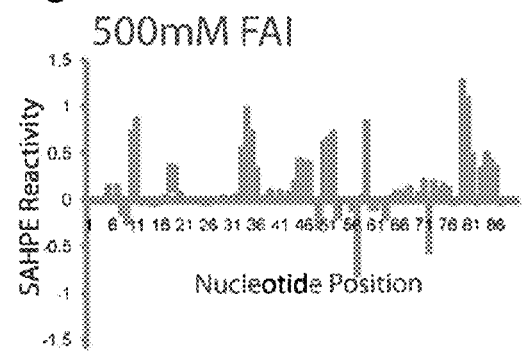
Figure 8G:
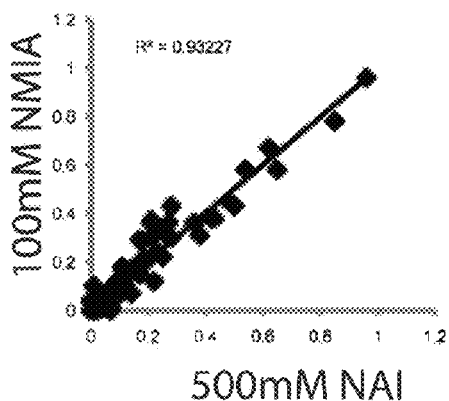
Figure 8E:
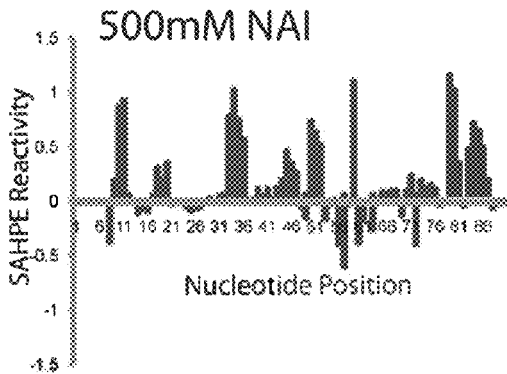
Figure 8H:
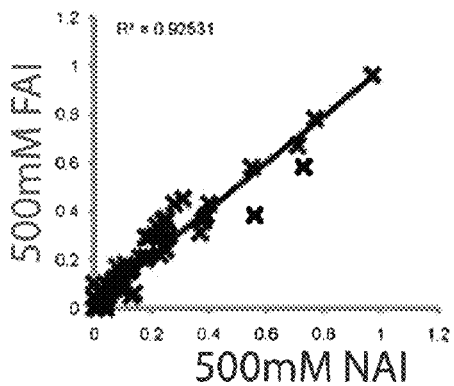

Quenching of acylation reaction. Addition of beta-mercaptoethanol (B-Me) according to the method described above halted the gel shift acylation reaction as illustrated in FIG. 7.

Secondary structure of human 5S rRNA in vitro. 5S rRNA was selected because of its abundant nature, highly characterized structure, and ability to fold into a stable structure without the need for protein cofactors. Similar quantitative patterns of 2'-hydroxyl acylation with NAI or FAI versus NMIA were observed (e.g., $R^2$=0.93, FIG. 1D and FIG. 8). The reactivities of the probes were mapped to the predicted secondary structure of human 5S rRNA. Modifications by NMIA, FAI and NAI all map to residues that are predicted to be flexible (FIG. 1B and FIG. 8). These data suggest that both NAI and FAI are suitable electrophiles for 2'-hydroxyl acylation on structured RNA molecules, yielding accurate structural information.

Probing RNA in Live Cells

Figure 9:
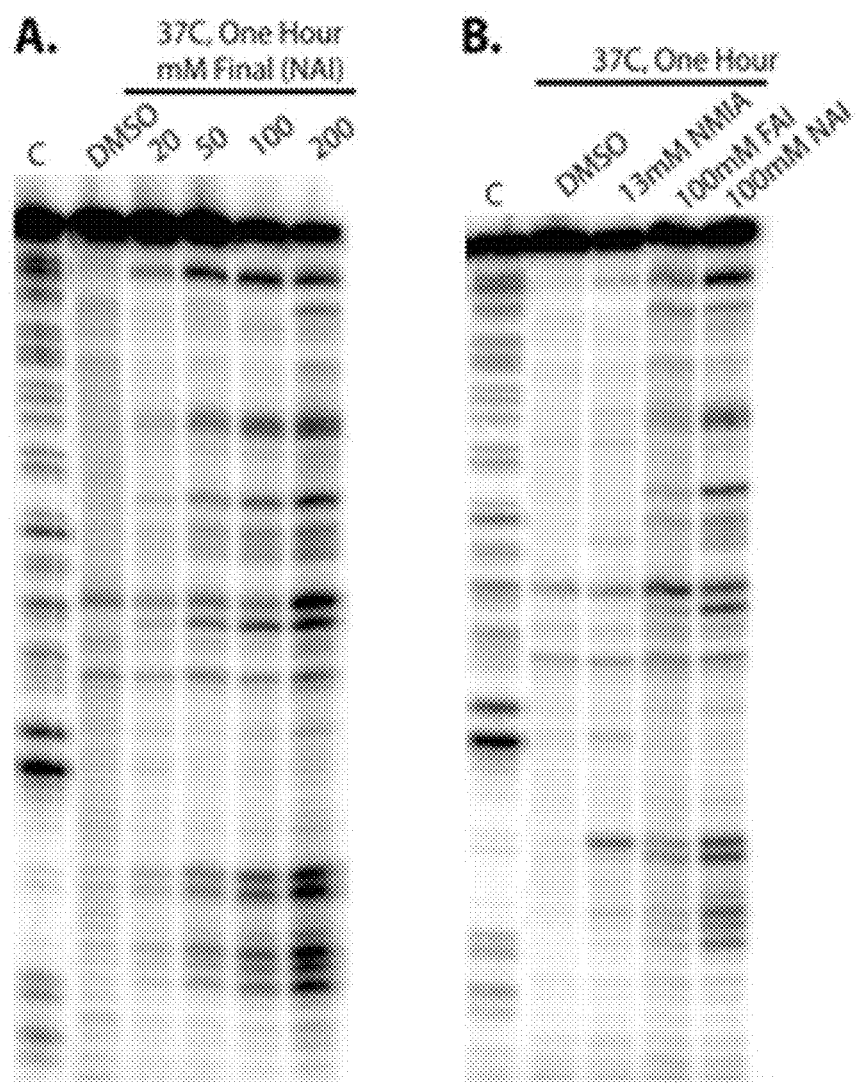
FIGS. 9A-9B illustrate gel shift results of probe reactivity with RNA in cells: (A) Increasing amounts of NAI yield concentration-dependent reverse transcription stops; and (B) Higher concentrations of NAI and FAI produce reverse transcription stops.

The ability of NAI and FAI to monitor RNA structure in live cells was evaluated. Cultured mouse embryonic stem cells (ESC) were reacted with NAI or FAI in aqueous buffer, using methods described above. At 13 mM probe (the maximum solubility of NMIA), no 5S rRNA modification was detected after one hour. At 20 mM probe, positive signals for modification were observed. Both NAI and FAI employed in the cellular experiments caused blocks in subsequent reverse transcription, suggesting modification, while NMIA did not (FIG. 9). In addition, NAI showed greater extent of modification than FAI, consistent with its higher reactivity toward ATP in vitro.

FIG. 9: Characterization of electrophile reactivity with RNA in cells. (A) Increasing amounts of NAI yield concentration-dependent reverse transcription stops. (B) Higher concentrations of NAI and FAI produce reverse transcription stops. At the solubility limit of NMIA there is no sign of modification, even on 5S rRNA, one of the most abundant transcripts in the cell. Notably, NAI gives higher intensity RT stops at the same concentration as FAI, which is consistent with its higher reactivity to ATP.

Figure 10:
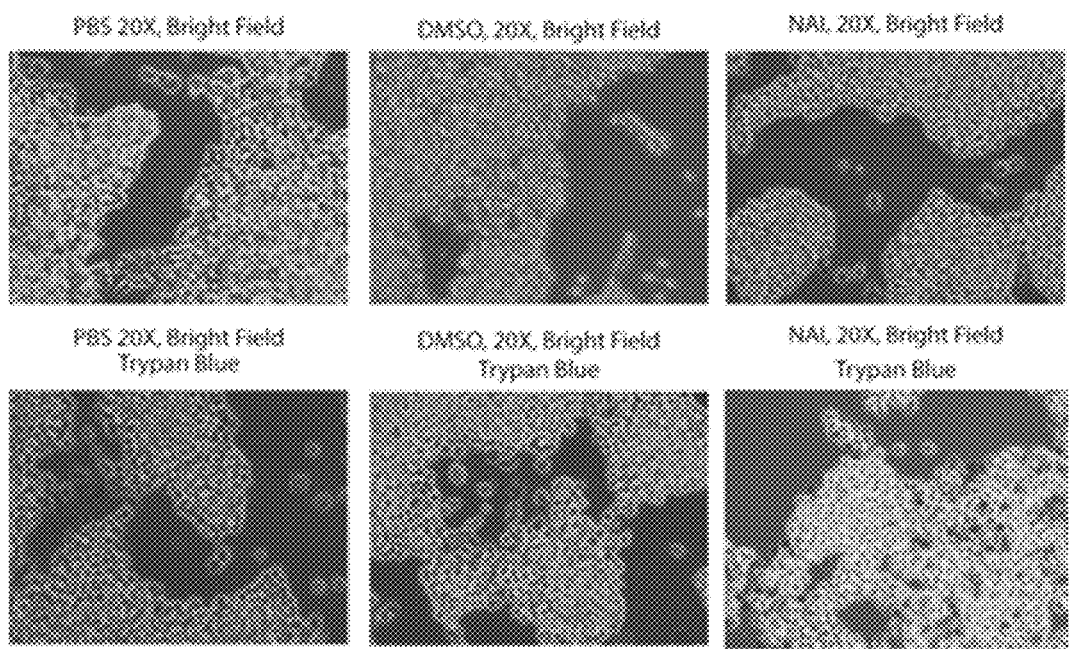
FIG. 10: Bright field imaging of V6.5 mESCs. Images show little evidence of membrane and cell morphology disruption during one hour when incubated with NAI or DMSO vehicle control as compared to PBS (TOP ROW). Even after 60 minutes of NAI treatment, ESCs remained attached to tissue culture vessel, appeared morphologically normal and unstained by trypan blue (BOTTOM ROW).

NAI probing of murine ESC. Application of 100 mM NAI to murine ESCs according to the methods described above, resulted in 5S rRNA modification in as little as one minute with suitable signal-to-noise ratio. This signal begins to plateau by 15 minutes (FIG. 10). Even after 30 minutes of NAI treatment, ESCs remained attached to tissue culture vessel, appeared morphologically normal and unstained by trypan blue (FIG. 10).

Figure 11A:
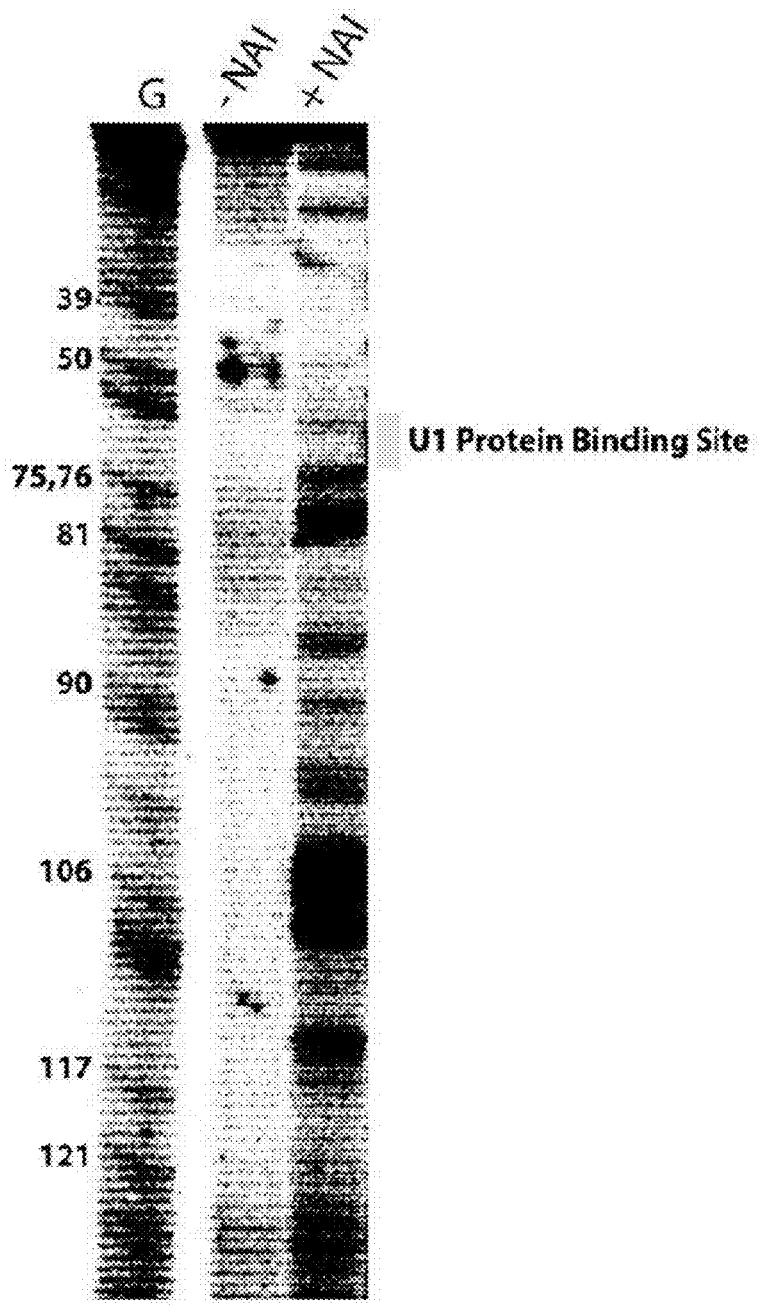
Figure 11B:
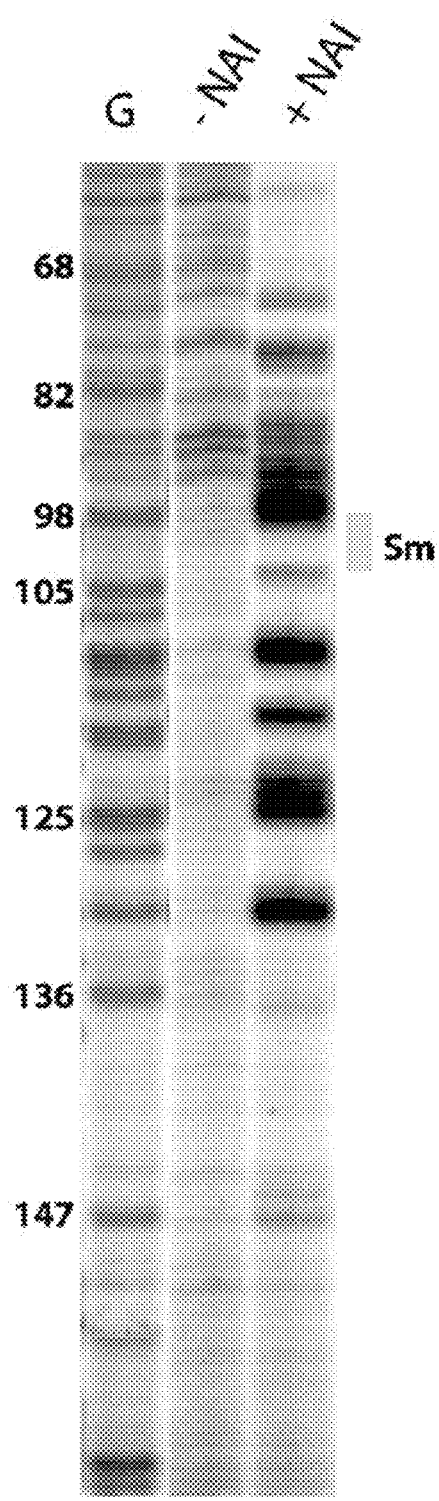
Figure 11C:
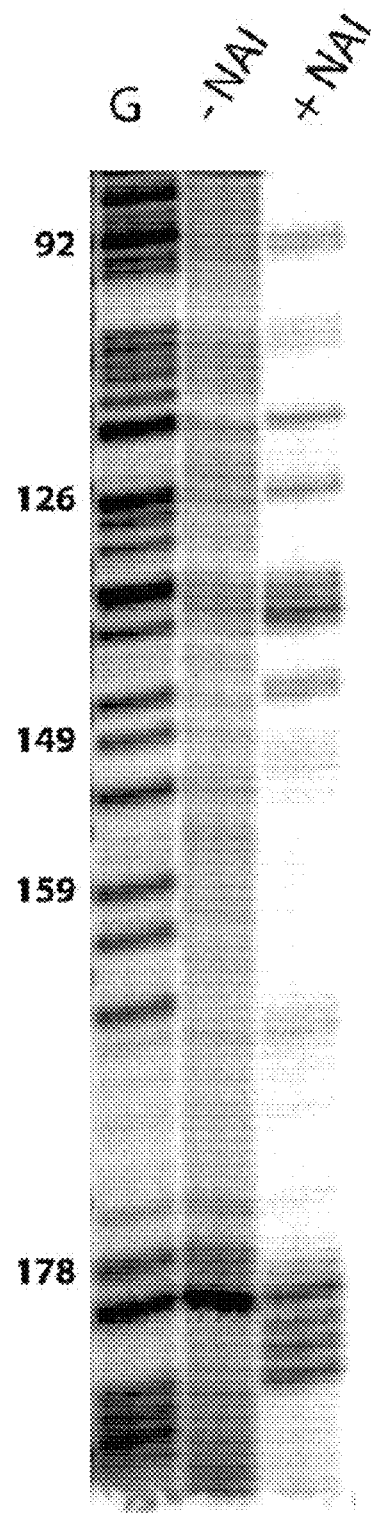

To test the ability of the probe reagent to modify lower abundant RNAs, the SHAPE pattern for three nuclear localized RNAs was determined. Significant RNA modification was detected which suggests that the reagent is able to enter the nucleus and react with lower abundant RNAs to give structural information (FIG. 11). NAI also modifies 5S rRNA in cultured human cancer cells, Drosophila S2 cells, yeast cells, and E. coli cells, suggesting that it is a general cell-permeable probe of RNA structure.

Figure 2A:
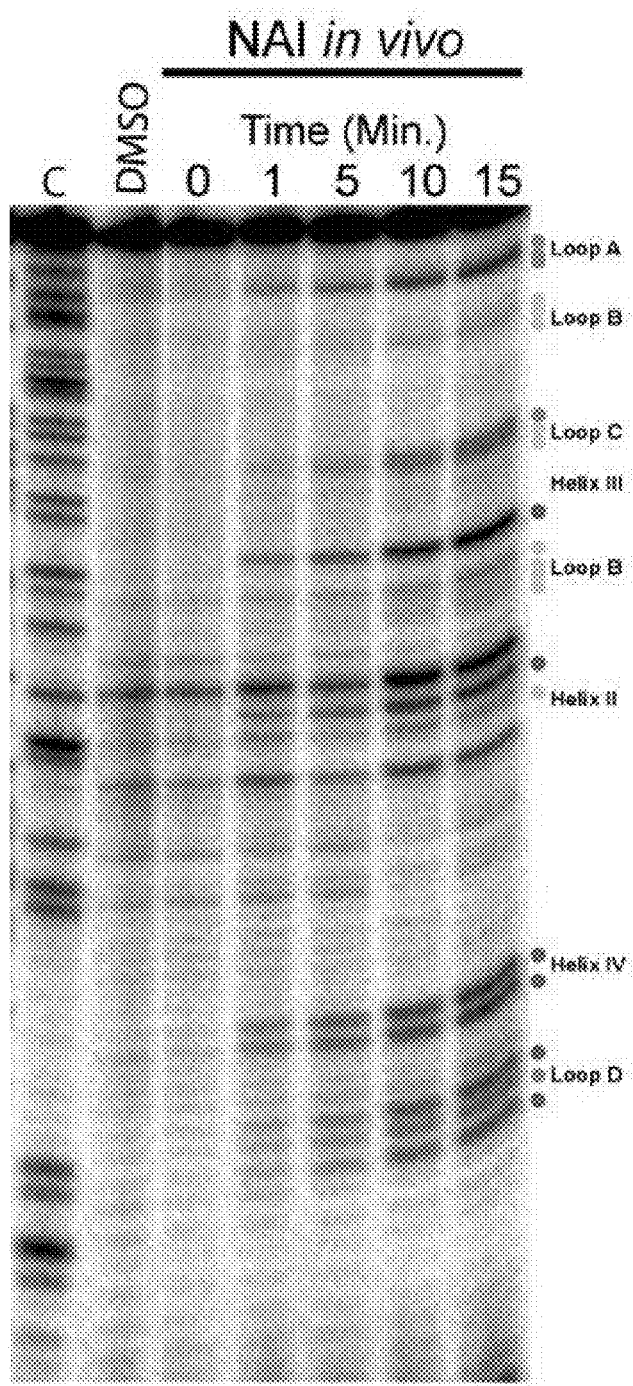
FIG. 2A-C shows a denaturing gel electrophoresis of NAI modification of 5S rRNA in cells (A). Also depicted is secondary structure mapping of NAI modification of 5S rRNA (SEQ ID NO: 15) in cells (B), and a three-dimensional model of S.C. 5SrRNA with modifications superimposed onto the structure (PDB 3U5H) (C).
Figure 2B:
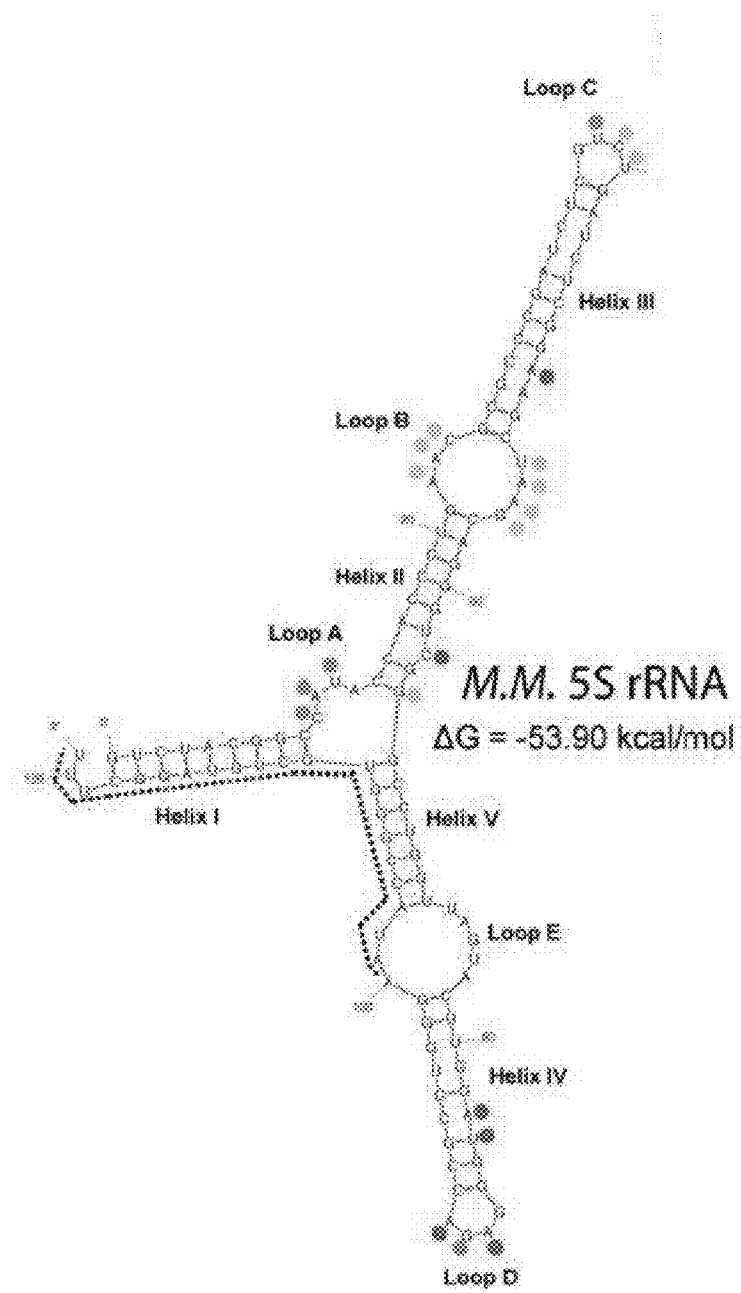
Figure 2C:
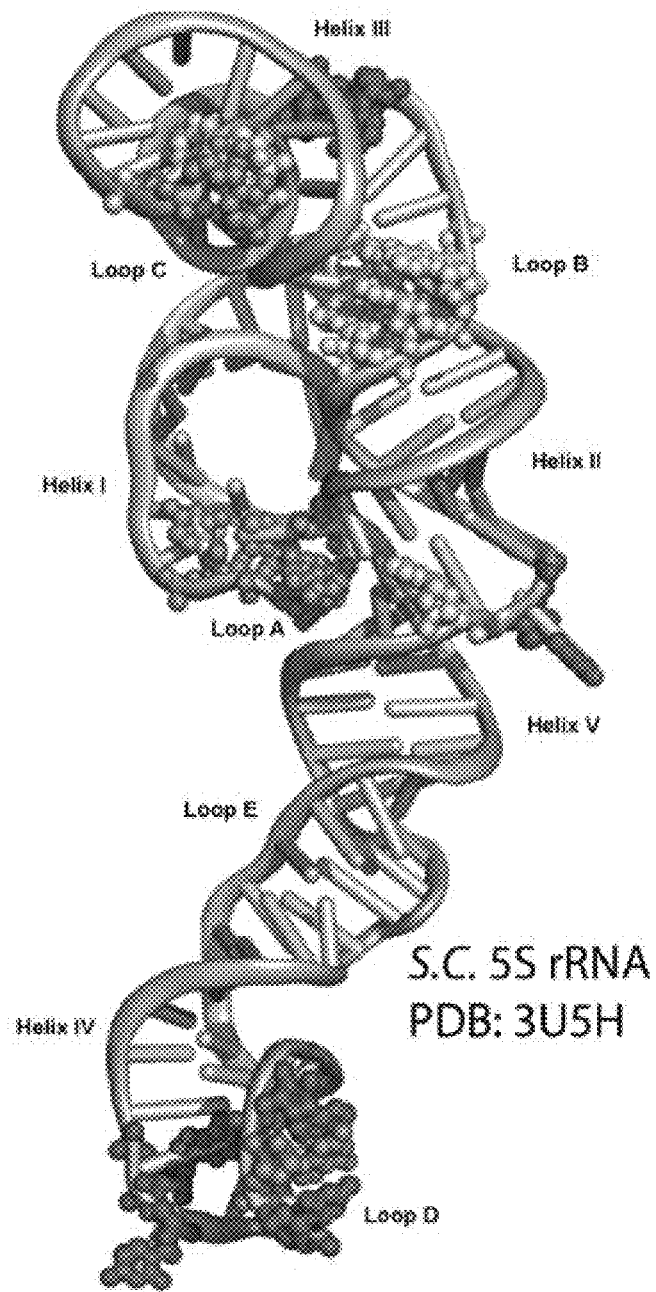

The pattern of 5S rRNA SHAPE in ESCs was compared to the crystal structure of the 80S ribosome from yeast, which includes the 5S rRNA (Ben-Shem, A. et al. The structure of the eukaryotic ribosome at 3.0 A resolution. Science 334, 1524-152, 2011). Yeast and mammalian 5S rRNA exhibit very high sequence similarity and functional domain architecture, as indicated by a CLUSTALW alignment score of 60. The crystal structure of the ribosome is validated by decades of molecular genetics and biochemical studies and likely represents a conformation that occurs in vivo. Overlaying the SHAPE data with the subject probes to the 5S crystal structure showed that practically all residues in flexible regions or not in canonical Watson-Crick base-pairs are modified, including single-stranded loops, unstable non-canonical base-pairs, and a single base flipped out of the helical duplex (FIG. 2). These results indicate that the subject reagents probe RNA structure in vivo with high accuracy and single-nucleotide resolution.

Comparison of SHAPE profiles of 5S rRNA in vivo versus in vitro reveal key RNA-RNA and RNA-protein interactions that dock the 5S rRNA into the ribosome. Overall, the profiles look similar, but a few key differences suggest differential interactions in the living system (FIG. 3, A and B). FIG. 3 illustrates that 5S rRNA has different modification patterns in cells: (A) Denaturing gel electrophoretic analysis of NAI modification of 5S rRNA in M. musculus Embryonic Stem cells and in vitro; and (B) Normalized Differential profile of M. musculus Embryonic Stem cell 5S rRNA.

Hereafter, residues in 5S are numbered per the mouse gene (M. musculus, M.M.); residues in other ribosomal subunits are numbered as in the yeast crystal structure (S. cerevisiae, S.C.). First, differences between the in vitro and in vivo modification profiles were observed with residue M.M.A49/M.M.A50. Within the context of the crystal structure it is noted that the analogous residue S.C.U51, which sits near the nexus of Loop B and Helix III, is kinked to allow the docking of Loop C into the 28S rRNA (Resi. S.C.C2684 and S.C.U2683). This conformation permits the residues S.C.ARG218, S.C.LEU222, S.C.GLU221, and S.C.LYS224 to be stacked against residues S.C.A51 and S.C.U50 (FIG. 4D). As a result, S.C.U51 seems to be pushed out of the helix, thus increasing its dynamic nature and exposing the 2'-OH for reactivity. Prior saturation mutagenesis showed that S.C.A51 and S.C.U50 make contact with ribosomal proteins S.C.L11 and S.C.L5 to form a critical structural link between the large and small ribosomal subunits and are essential for proper ribosome function and viability (Smith et al., Saturation mutagenesis of 5S rRNA in Saccharomyces cerevisiae. Mol Cell Biol 21, 8264-827, 2001; Yusupov et al. Crystal structure of the ribosome at 5.5 A resolution. Science 292, 883-896, 2001). Thus, the subject probes can read out alterations in the RNA tertiary structure as a result of sampling critical mature ribosome conformations.

Figure 4:
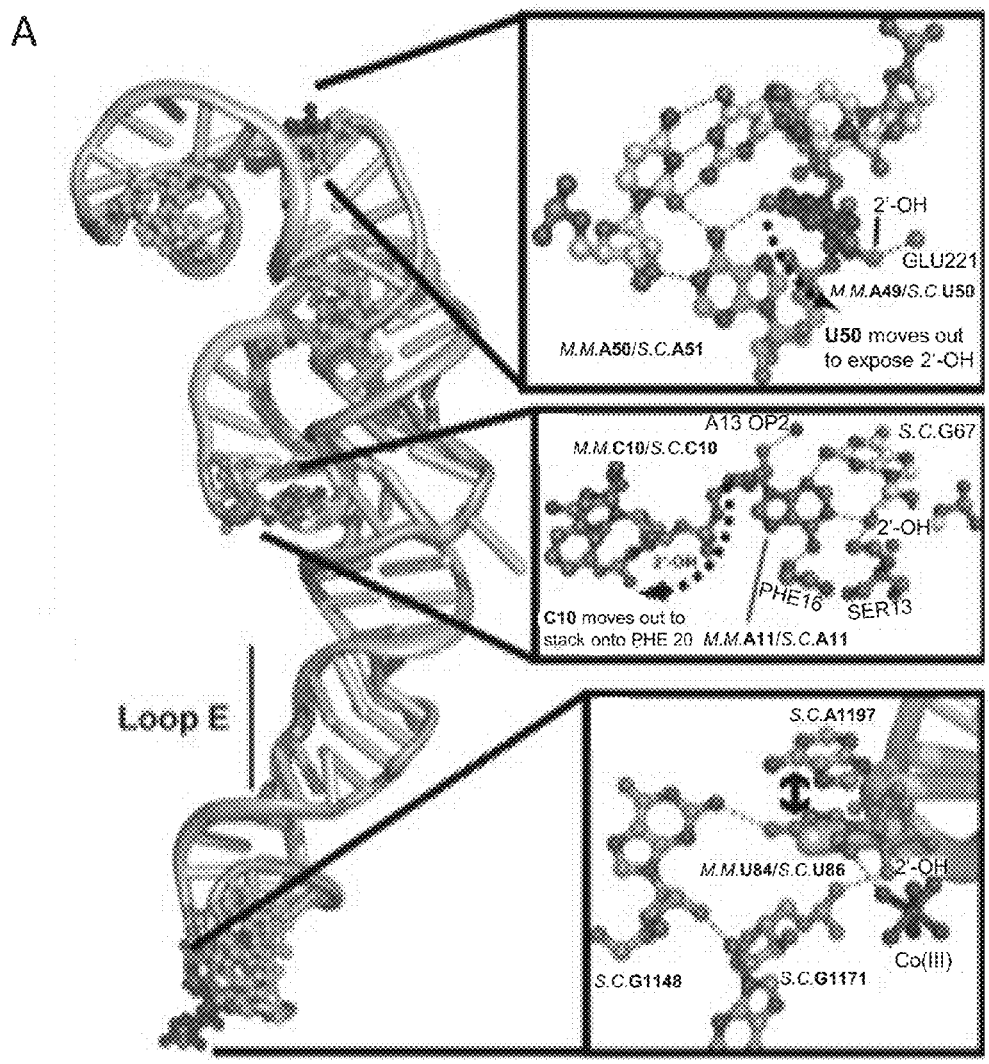
FIGS. 4A-4D: A. Three-dimensional model of S.C. 5SrRNA with differential modifications superimposed onto the structure (PDB 3U5H). (B) Closeup view of hyperreactivity of M.M. A49 and S.C. U50. U50 is near the kink of helix II and helix III, This conformation, which allows Loop C to interact with 28S rRNA promotes the ejection of S.C. U50 2'-OH thus rendering it more dynamic and reactive to NAI modification. (C) Zoomed-in view of a three-nucleotide bridge that joins loop A to helix II. This conformation results in docking of A11, hiding its 2'-OH through a hydrogen bond with A13-OP2. In addition C10 is forced into a stacking interaction with PHE20, which exposes the 2'-OH, potentially increasing its reactivity with NAI. (D). Close up view of differential modification of Helix IV. The ribosome crystal structure shows many of the residues that are hypomodified in cells are engaged in extensive interactions with ribosomal RNA. Shown is the interaction of U86 with 28S rRNA. Such extensive bonding and stacking may be stabilizing the internucleotide linkages of these residues, limiting their acylation reactivity.
Figure 6A:
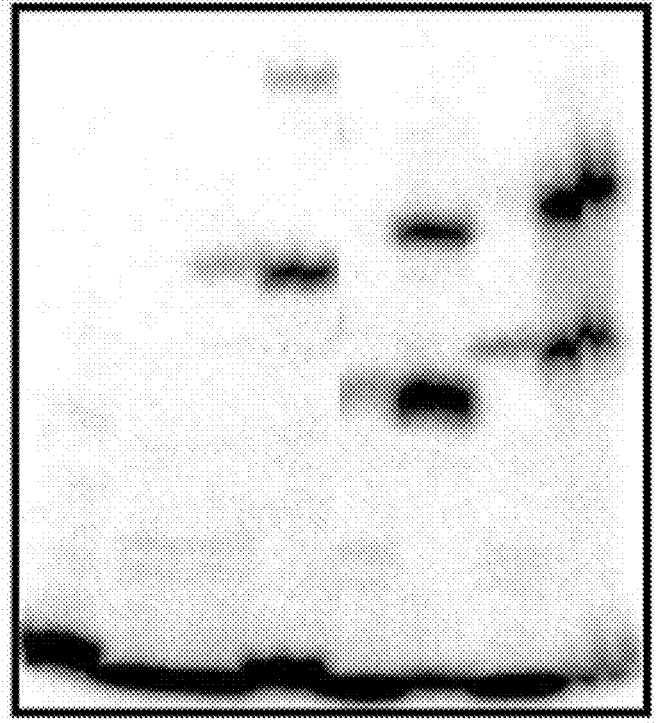

Second, a three-nucleotide bridge that connects Helix II with Loop A (M.M.C10, M.M.U11, and M.M.G67) showed significant differences (FIG. 4, panel C). Within the crystal structure S.C.C10, S.C.A11, S.C.G67 are engaged in a three-nucleotide bridge. S.C.G67 and S.C.A11 are involved in extensive hydrogen bonding interactions that may stabilize them in lower-reactive conformations. S.C.C10 also moves out of the helix to stack on S.C.PHE20. This conformation exposes the 2'-OH of S.C.C10 and may result in increased reactivity to NAI in vivo.

Third, the residues of M.M.U84/M.M.A83, which are in Loop D, were more reactive to NAI in vitro. Within the context of the 80S ribosome these residues are engaged in extensive hydrogen-bond contacts with residues S.C.G1148 and S.C.G1171 of 28S S.C.rRNA. S.C.U86 is stacked upon S.C.A1197 and is in an H-bonding contact with cobalt hexamine (FIG. 4, panel D). Notably, mutations of these 5S residues in yeast result in gross defects in translational accuracy. These differences suggest that NAI is able to distinguish subtle dynamic differences that may be the result of protein interactions, yet can still identify residues that are unpaired and therefore more flexible in the context of the cell. These findings suggest in vivo versus in vitro SHAPE comparison as a powerful unbiased strategy to pinpoint key residues in ncRNA interaction and function.

Comparison of the predicted RNA secondary structure and the present data showed that the subject reagent was unable to produce significant modification patterns from residues in Loop E in the M.M. 5S pattern. Existing reagents also failed to probe Loop E in vitro, and its high degree of hydrogen bonding and stacking interactions that are thought to prevent Loop E residues from interacting with single-strand specific reagents and RNases. Loop E was slightly more reactive to NAI in vitro, and these residues are completely devoid of modification in vivo. This result is surprising because the S.C. crystal structure showed two residues, C72 and C73, to be pushed out of Loop E. These residues also have the highest b-factor, suggesting these residues are highly dynamic (FIG. 5G). Analysis of in vitro and in vivo modified 5S rRNA in yeast revealed several residues with similar modification patterns as in the mouse 5S rRNA. Further, residues with lower b-factors in the crystal structure were shown to be less reactive in vivo. Importantly, residues C72 and C73 displayed the largest differences in the cell, with a marked increase in reactivity (FIG. 5, panels B and C). Moreover, residues with altered modification pattern in vivo are often required for 5S function in vivo when mutated (FIG. 5, panel C).

These results show that the subject probes are able to distinguish functional RNA dynamics that are the result of a mature cellular complex, and can be used to compare X-ray structures to interrogate cellular RNA complexes. This analysis is the first comparison of 5S rRNA structure in vitro versus in vivo. Overall, these experiments establish that the subject acylation reagents are capable of modifying RNA in vivo and can sensitively read characteristics of RNA structure that are the result of unique conformations that RNA adopts in the cell.

Figure 12:
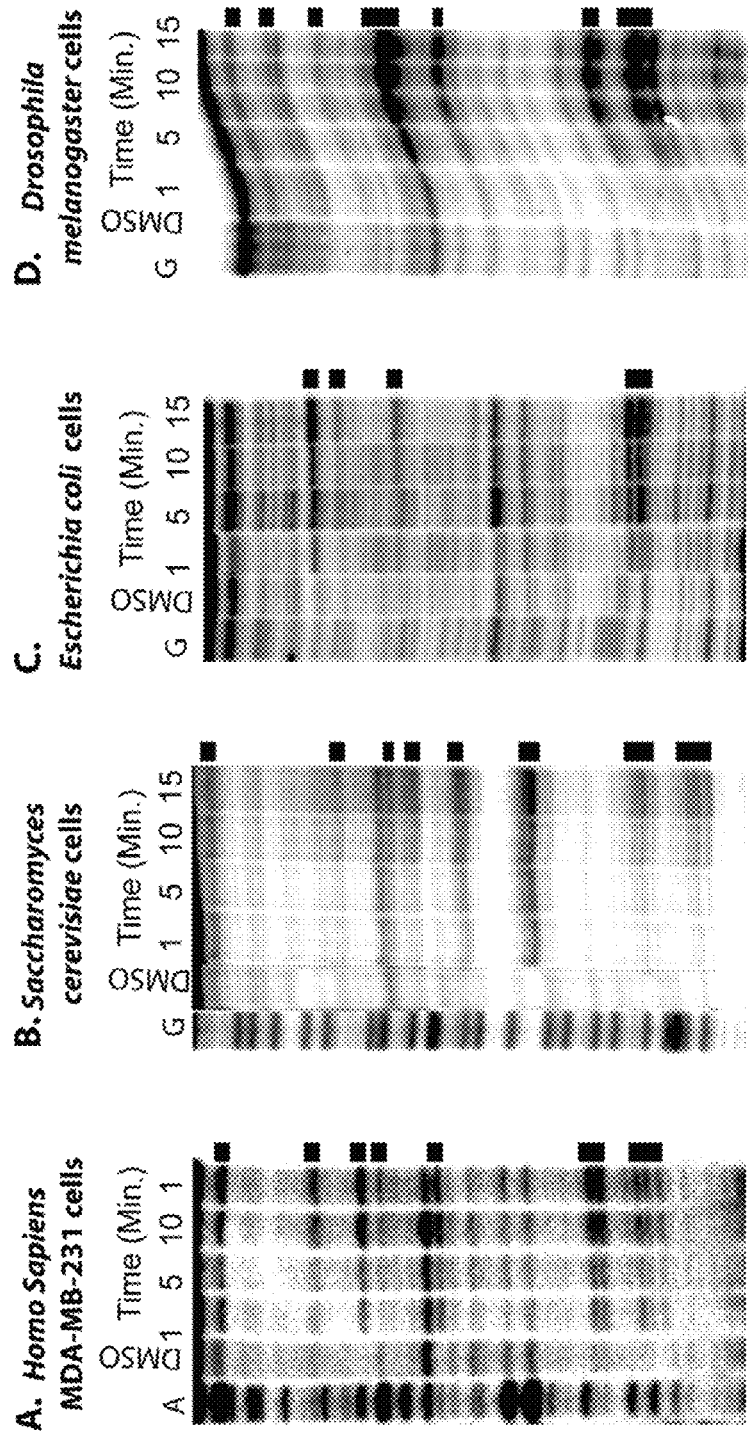
FIGS. 12A-12D illustrate the results of acylation reactions using NAI with denaturing gel electrophoresis: (A) *Homo sapiens* MDA-MB-231 cells 5SrRNA RT products; (B) *Saccharomyces cerevisiae* cells 5S rRNA RT products; (C) *Escherichia coli* cells 5S rRNA RT products; (D) *Drosophila melanogaster* cells 5S rRNA RT products.

Modification of cellular RNA from several species. FIG. 12 illustrates the results of acylation reactions using NAI with denaturing gel electrophoresis: (A) Homo sapiens MDA-MB-231 cells 5SrRNA RT products; (B) Saccharomyces cerevisiae cells 5S rRNA RT products; (C) Escherichia coli cells 5S rRNA RT products; (D) Drosophila melanogaster cells 5S rRNA RT products.

Figure 13:
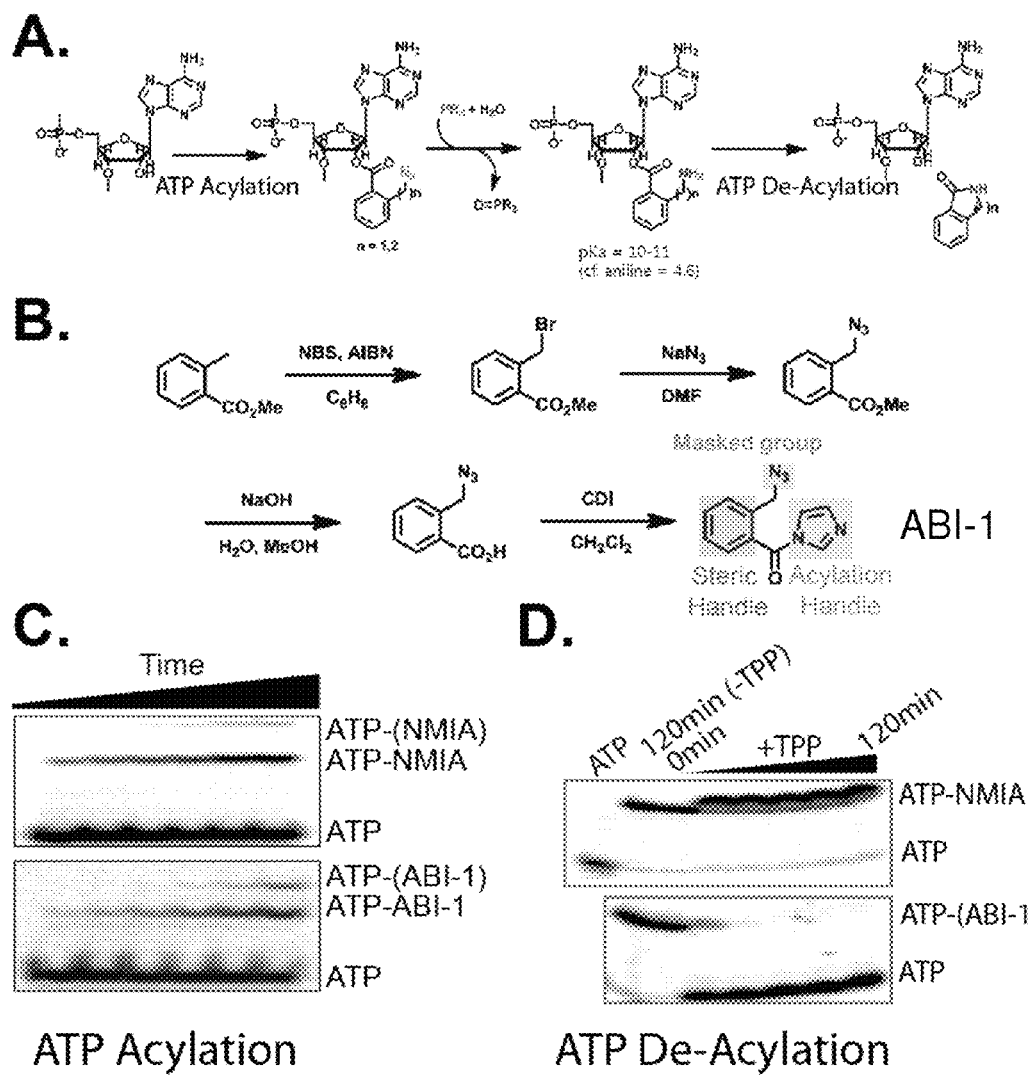
FIGS. 13A-13D illustrate the mechanism of action (A), synthesis (B) and evaluation (C-D) of a reversible acylation probe.

Synthesis and evaluation of azido containing probes. Azido containing probes are prepared according to the synthetic scheme shown in FIG. 13B. ABI-1 (FIG. 13B) was prepared starting with commercially available methyl 2-methylbenzoate. The compounds are screened to optimize two parameters: acylation time and solubility. ABI-1 satisfied these criteria with medium solubility (20 mM, 10% DMSO) and similar kinetics of acylation of ATP as compared to the anhydride reagent NMIA (FIG. 13C). These data show that ABI-1 is a suitable electrophile for 2'-hydroxyl acylation.

The isolated ATP-(ABI-1) adducts were incubated with a series of triarylphosphine compounds at room temperature. ATP was quantitatively deacylated in as little as 15 minutes and NMIA, a negative control, was not (FIG. 13D). ABI-1 probes are removed from RNA without compromising the integrity of the RNA itself. Together, these results demonstrate the feasibility of the catch-and-release RNA modification protocol.

Figure 14B:
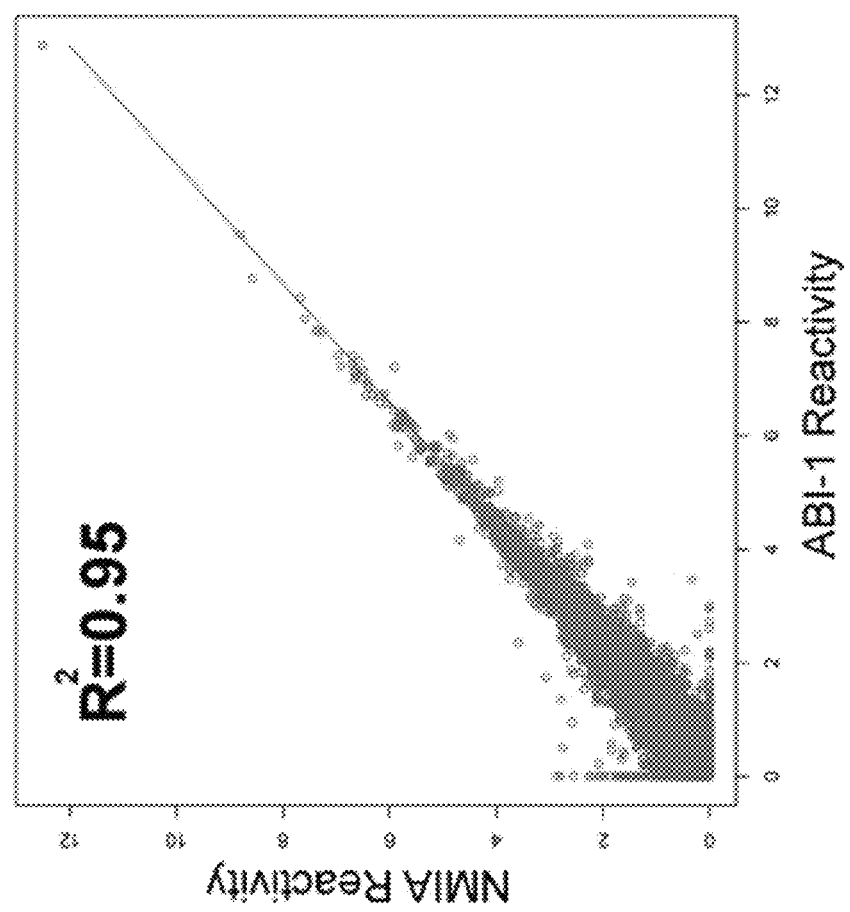
FIGS. 14A-14B illustrate the results of secondary structure mapping of HOTAIR RNA using the reversible RNA probe ABI-1: (A) Gel electrophoresis of cDNA products; and (B) Correlation between 2'-OH reactivity to NMIA and ABI-1.
Figure 14A:
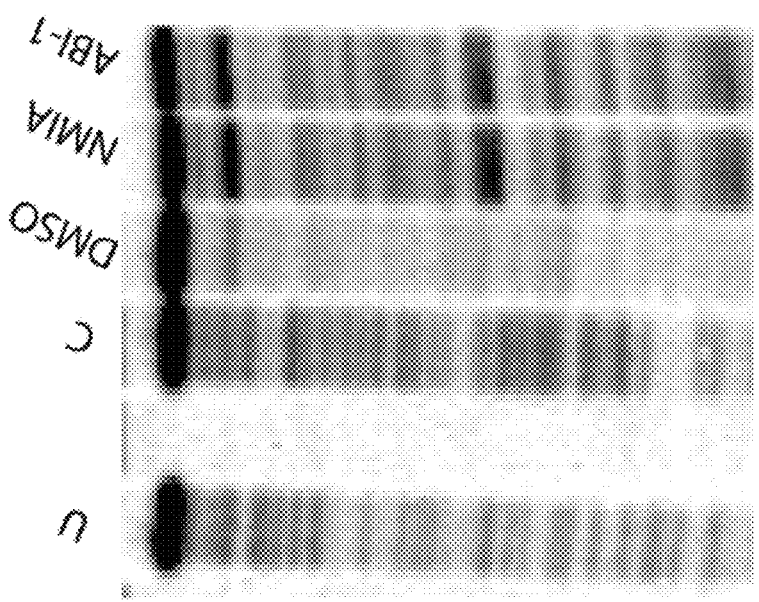

ABI-1 as a probe of RNA secondary structure. To evaluate the compound's ability to modify RNA at conformationally flexible positions ABI-1 was tested in comparison to NMIA. ABI-1 and NMIA were incubated with in vitro transcribed RNA and with DMSO as a negative control. After incubation, the RNA was extracted and precipitated with ethanol. The resuspended RNA was then reverse transcribed with a radiolabeled primer and cDNA products were analyzed on a sequencing gel (FIG. 14A). As shown in FIG. 14, A and B there is little difference between the cDNA products created from ABI-1 treated RNA and RNA exposed to NMIA. Both reagents successfully mapped the predicted secondary structure of the 5' end of HOTAIR, a long non-coding RNA. Overall, these results establish the reversible modification strategy to accurately measure RNA secondary structure.

Figure 15:
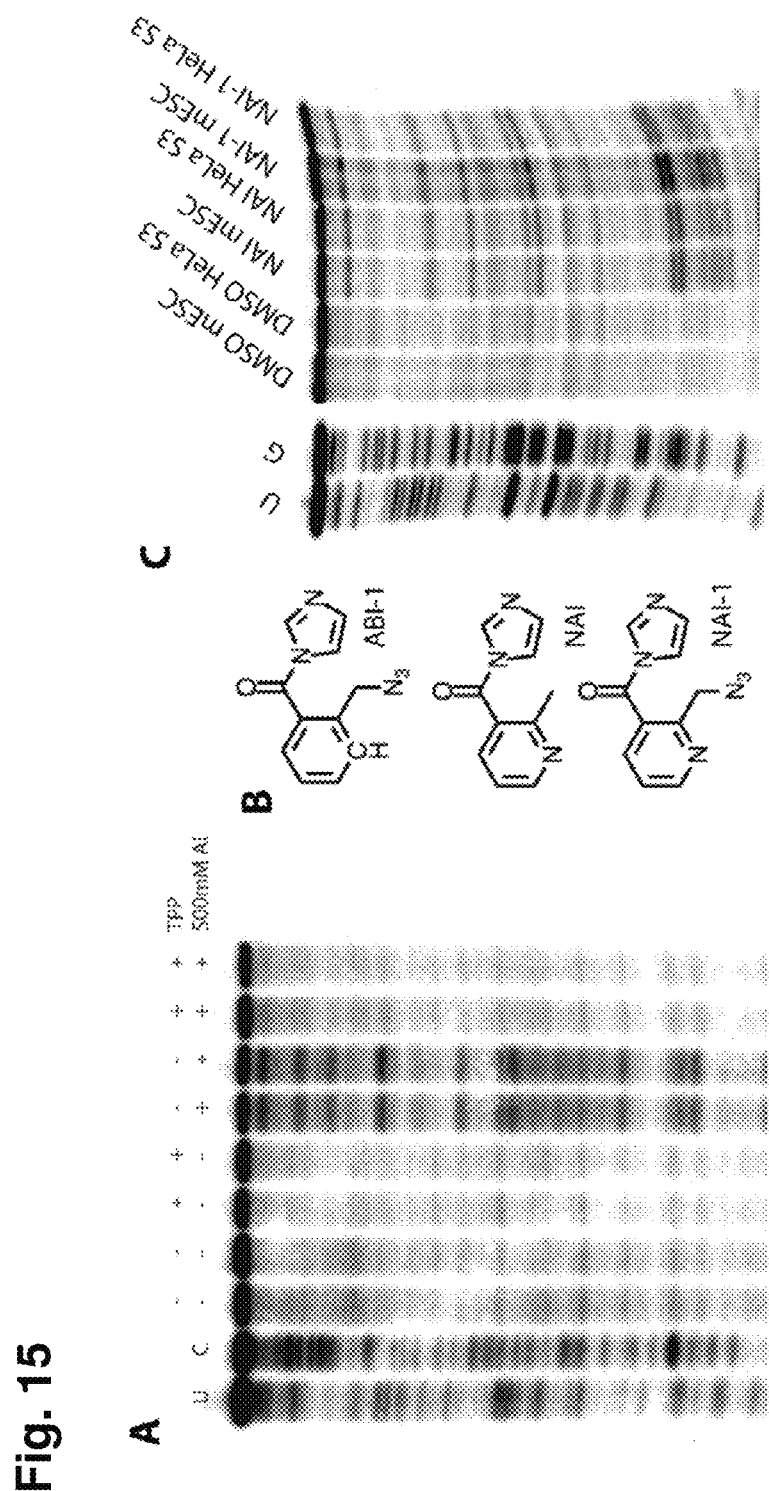
FIGS. 15A-15C illustrate reversible acylation of RNA and cell permeability of reversible acylation probes: (A) Gel electrophoresis of cDNA products using ABI-1, with and without triphenylphosphine (TPP); (B) Chemical structures of ABI-1, NAI, and NAI-1; (C) structural modification of RNA in various cells using NAI-1.

ABI-1 Reversible Modification and Cell-Permeability. The ability of ABI-1 to reversibly acylate RNA, without compromising the integrity of the full-length transcript was investigated. ABI-1 is incubated with in vitro transcribed RNA (+) and with DMSO as a negative control (−). After incubation the RNA is extracted and precipitated with ethanol. The RNA is then subjected to deprotection conditions (80° C., 20 minutes and 16 mM triphenylphosphine (TPP)). The RNA is then precipitated and the resuspended RNA is then reverse transcribed with a radiolabeled primer and cDNA products are analyzed on a sequencing gel (FIG. 15, A). The results showed that in the presence of TPP the RNA is deprotected, (see e.g., FIG. 13D), without compromising the integrity of the RNA itself. Nicotinic acid derivative NAI-1 was evaluated for permeating cell membranes and reading out RNA secondary structure accurately (see FIG. 15C). The data shows that NAI-1 was able to read RNA secondary structure and permeate cells. FIG. 15A. Demonstration of RNA deprotection with ABI-1; FIG. 15B. Chemical structures of ABI, NAI, and NAI-1; FIG. 15C. Demonstration of cell-permeability and structural modification of RNA in cells using NAI-1.

Figure 16D:
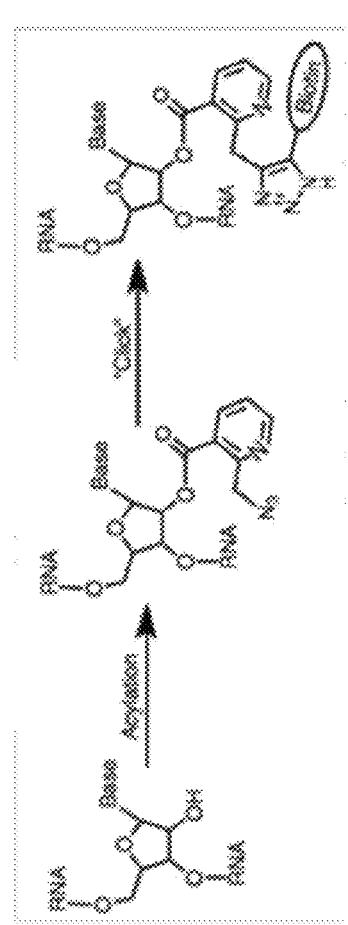
Figure 16E:
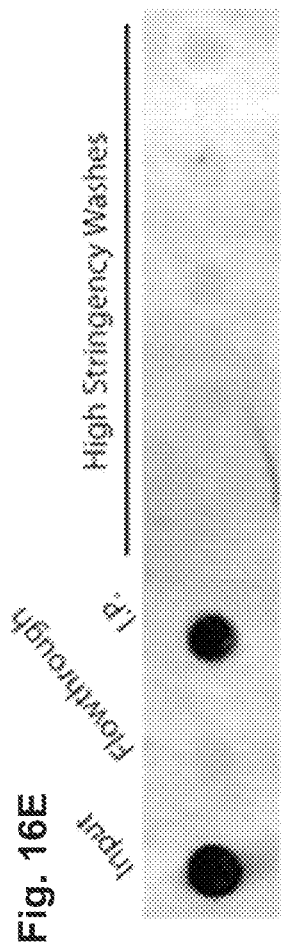
Figure 16C:
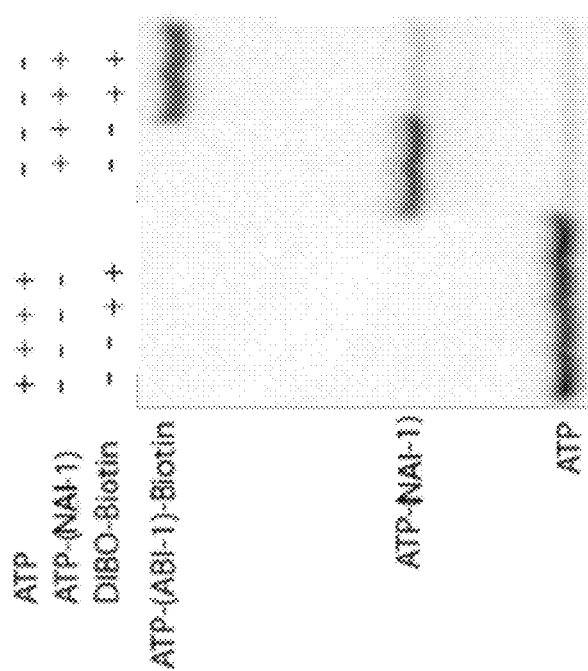

Tagging Acylation Chemicals Through "Click" Chemistry (FIG. 16). The compound NAI-1 was used for conjugation to both fluorophores and enrichment handles using "click" chemistry. Using the azide-linked acylation reagent we have been able to link fluorescent dye to NAI-1/RNA complexes. We used DIBO-click for copper-free chemistry to conjugate to RNA (Summarized in FIG. 16, A and B). These results suggest that these reagents can be conjugated to fluorescent markers for RNA labeling in solution. We also have been able to demonstrate RNA conjugation to a solid-phase resin, as is shown by depletion of click-fluorophore signal (FIG. 16, B; lane 3 and 4).

We have also demonstrated that NAI-1 can be used to tag RNAs with an enrichment handle and that this tagging is dependent on the azide acylation handle. As shown in FIG. 16, C we can acylate hydroxyls from ATP (an acylation mimic of RNA). We can also supershift the acylated ATP with copper free "click" chemistry with DIBO-biotin. The scheme is outlined in FIG. 16, D. We were also able to show that we can isolate biotin-conjugated RNAs using a pull-down. We can show enrichment for biotin labeled RNAs using a streptavidin pulldown in which the isolated RNAs are eluted then probed using a streptavidin dot-blot (FIG. 16, E). Together these results demonstrate that NAI-1, or other azide functionalized acylation chemicals can be functionalized after their conjugation to RNA.

Enriching for Acylated RNAs to Decrease Background in RNA Structure Probing Experiments. Using conditions discussed in FIG. 16, we can enrich for RNAs that have been acylated with NAI-1. We then tested the ability of this enrichment strategy to isolate RNA structure signatures associated with acylation.

In a given RNA structure probing experiment the amount of RNA that is acylated under single-hit kinetics is ~15-20% of the total RNA. This can often result in a substantial amount of background that results from either spurious RT stops or full-length cDNAs that arise from reverse-transcription on unmodified RNAs. As shown in FIG. 17, we have been able to isolated purified RNAs (IP lane) that map back to segments of RNA we predict to be acylated (single-stranded regions, denoted with orange circles). We also de-enrich for spurious stops that map to known double stranded regions (double-stranded regions, denoted with blue circles). This enrichment is also dependent on our acylated RNAs being functionalized with biotin through our copper-free "click" chemistry (−biotin vs +biotin; FIG. 17, A). We also significantly de-enrich for full-length cDNAs; the full-length band for un-modified cDNAs is outlined in red. Overall, this data suggest were are able to isolate acylated RNAs and wash away RNAs that are unmodified, further demonstrating the feasibility of labeling and manipulating RNA with through our novel reagents.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for obtaining structural data from a RNA in a sample, the method comprising:
   contacting the sample with a SHAPE probe to acylate one or more unconstrained nucleotides of the RNA to produce a 2'-acylated RNA, wherein the SHAPE probe is described by formula (II):

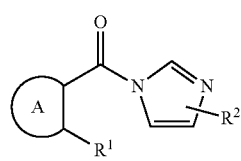

wherein:
   A is selected from a phenyl, a pyridyl, a pyrrolyl, a furanyl, a thienyl, a thiazolyl, an imidazolyl, an oxazolyl, a pyrimidinyl, a pyrazinyl and a pyridazinyl ring;
   $R^1$ is H or a lower alkyl;
   $R^2$ is H or a lower alkyl; and
   analyzing the 2'-acylated RNA to obtain structural data.
2. The method of claim 1, wherein A is substituted with a detectable label or a bioorthogonal functional group.
3. The method of claim 1, wherein the SHAPE probe is described by one of the following structures:

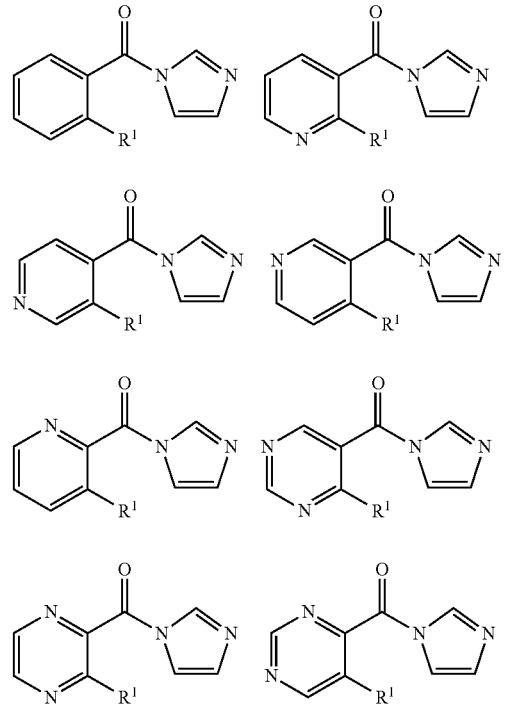

-continued

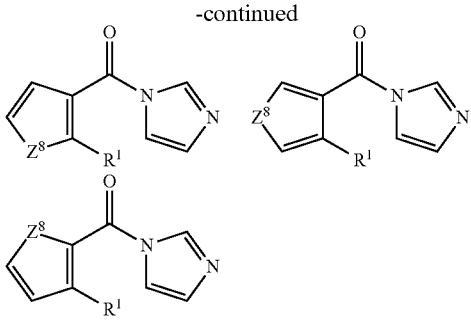

wherein:
Z$^8$ is O, S or NR$^4$, wherein R$^4$ is H or a lower alkyl; and R$^1$ is a lower alkyl.

4. The method of claim 3, wherein R$^1$ is methyl.

5. The method of claim 3, wherein R$^1$ is selected from one of the following groups:

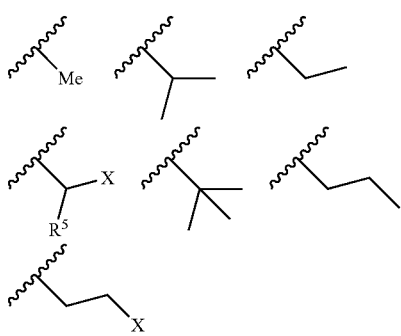

wherein X is selected from —N$_3$, hydroxyl, protected hydroxyl, protected thiol, amino and protected amino; and
R$^5$ is H or an alkyl group substituent.

6. The method of claim 5, further comprising applying a stimulus to the sample to de-acylate the 2'-acylated RNA.

7. The method of claim 6, wherein the stimulus is a photon, a deprotection reagent or an azido-reactive agent.

8. The method of claim 7, wherein:
R$^1$ is —CH$_2$—N$_3$ or —CH$_2$CH$_2$N$_3$; and
the stimulus is selected from an arylphosphine, an alkylphosphine, an arylalkylphosphine and a dithiol.

9. The method of claim 2, wherein A is substituted with the bioorthogonal functional group and the method further comprises:

contacting the sample with a modifying reagent under conditions sufficient to conjugate the reagent to the bioorthogonal functional group of the A ring of a 2'-acylated RNA.

10. The method of claim 9, wherein the modifying reagent is selected from a a detectable label reagent comprising a fluorophore or a peptide tag and a solid support.

11. The method of claim 1, wherein the sample is a cell.

12. The method of claim 1, wherein the sample is in vivo.

13. The method of claim 1, wherein the sample is in vitro.

14. The method of claim 3, wherein the SHAPE probe is described by one of the following structures:

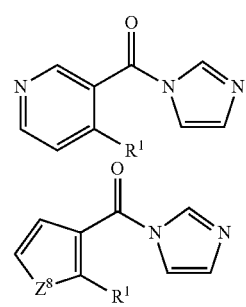

wherein Z$^8$ is O.

15. The method of claim 13, wherein the SHAPE probe is:

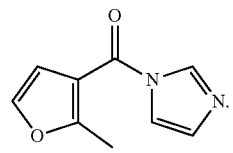

16. The method of claim 13, wherein the SHAPE probe is:

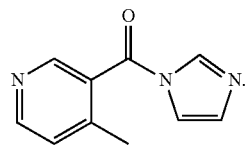

* * * * *